(12) United States Patent
Knox et al.

(10) Patent No.: US 6,740,748 B1
(45) Date of Patent: May 25, 2004

(54) DEVELOPMENTAL REGULATION IN ANTHER TISSUE OF PLANTS

(75) Inventors: Robert Bruce Knox, North Balwyn (AU); Mohan Bir Singh, Templestowe (AU); Huiling Xu, Coburg (AU)

(73) Assignee: The Univeristy of Melbourne, Victoria (AU)

( * ) Notice: Subject to any disclaimer, the term of this patent is extended or adjusted under 35 U.S.C. 154(b) by 0 days.

(21) Appl. No.: 08/454,294

(22) PCT Filed: Dec. 16, 1993

(86) PCT No.: PCT/AU93/00657

§ 371 (c)(1),
(2), (4) Date: Aug. 7, 1995

(87) PCT Pub. No.: WO94/13809

PCT Pub. Date: Jun. 23, 1994

(30) Foreign Application Priority Data

Dec. 16, 1992 (AU) ................................................ 6400/92

(51) Int. Cl.[7] ........................ C12N 15/29; C12N 15/82; C12N 5/04; A01H 5/00
(52) U.S. Cl. ..................... 536/23.6; 536/24.1; 800/287; 800/303; 800/306; 435/69.1; 435/468
(58) Field of Search ............................. 536/23.6, 24.1, 536/24.5; 435/172.3, 69.1, 205, 468; 88/205, DIG. 15, 17, 43, 58; 47/DIG. 1; 800/287, 303, 306

(56) References Cited

FOREIGN PATENT DOCUMENTS

| EP | 0 420 819 | 4/1991 |
|---|---|---|
| WO | WO90/08828 | 8/1990 |
| WO | WO92/13957 | 8/1992 |

OTHER PUBLICATIONS

Napoli et al. 1990. Plant Cell 2:279–289.*
Aarts et al. (1993) "Transposon Tagging of a Male Sterility Gene in Arabidopsis" *Nature* 363:715–717.
Theerakulpisut et al. (1991) "Isolation and Developmental Expression of Bcp1 and Anther–Specific cDNA Clone in *Brassica campestris*" *The Plant Cell* 3:1073–1084.
Mariani et al. (1990) "Engineered Male Sterility of Crops" *J. Cell. Biochem.* 14E:262 (Abstract R009).
Leemans et al. (1992) "Genetic Engineering for Fertility Control" *Plant* 28(3):51A (Abstract P–3).
Mariani et al. (1990) "Induction of Male Sterility in Plants By a Chimaeric Ribonuclease Gene" *Nature* 347:737–741.
Xu, Huiling et al. (1993) "Haploid and Diploid Expression of a *Brassica campestris* Anther Specific Gene Promotor in Arabidopsis and Tobacco" *Mol. Gen. Genet.* 239:58–65.
Diego Albani, et al. (1990) "Characterization of a Pollen–specific Gene Family from *Brassica napus* which is Activated during Early Microspore Development", *Plant Molecular Biology, 15*: 605–622.

Diego Albani, et al. (1991) "A Gene Showing Sequence Similarity to Pectin Esterase is Specifically Expressed in Developing Pollen of *Brasica napus*. Sequence in its 5' Flanking Region are Conserved in Other Pollen–specific Promoters", *Plant Molecular Biology, 16*: 501–513.

M.P. Alexander, (1969) "Differential Staining of Aborted and Nonaborted Pollen". *Stain Technology, 44* (3): 117–122.

Jim Haseloff, et al. (1988) "Simple RNA Enzymes with New and Highly Specific Endoribonuclease Activities", *Nature, 334*: 585–591.

Richard A. Jefferson, et al. (1987) "GUS Fusions: β–glucuronidase as a Sensitive and Versatile Gene Fusion Marker in Higher Plants" *The EMBO Journal, 6* (13): 3901–3907.

Anna M. Koltunow, et al. (1990) "Different Temporal and Spatial Gene Expression Patterns Occur during Anther Development", *The Plant Cell, 2*: 1201–1224.

Csaba Koncz, et al. (1986) "The Promoter of $T_L$–DNA Gene 5 Controls the Tissue–specific Expression of Chimaeric Genes Carried by a Novel Type of Agrobacterium Binary Vector", *Mol. Gen. Genet., 204*: 383–396.

Joseph P. Mascarenhas, "Anther–and Pollen–Expressed Genes", State University of New York at Albany, Chapter 6:, 97–115.

Barbara Moffatt, et al. (1988) "Positive Selection for Male–Sterile Mutants of Arabidopsis Lacking Adenine Phosphoribosyl Transferase Activity", *Plant Physiol. . , 86*: 1150–1154.

David Twell, et al. (1989) "Isolation and Expression of an Anther–specific Gene from Tomato" *Gen Gene, 217*:240–245.

David Twell, et al. (1990) "Promoter Analysis of Genes that are Coordinately Expressed During Pollen Development Reveals Pollen–Specific Enhancer Sequences and Shared Regulatory Elements", *Genes & Development, 5*:496–507.

* cited by examiner

*Primary Examiner*—David T. Fox
(74) *Attorney, Agent, or Firm*—Scully, Scott, Murphy & Presser

(57) ABSTRACT

The present invention relates generally to the use of genetic engineering to induce developmental regulation in anther tissue of plants, and more particularly to induce nuclear male sterility, and to genetic sequences useful for same. More particularly, the present invention relates to the identification of a genomic clone and promoter capable of tissue- and development-specific expression which provides a means of tissue and developmental regulation in plants and more specifically a means of producing nuclear male sterile plants. Even more particularly, the present invention provides a genomic clone having a nucleotide sequence as set forth in SEQ ID NO. 1 or homologous sequences thereof such as the nucleotide sequence as set forth in SEQ ID NO. 3.

7 Claims, 22 Drawing Sheets

```
TATCATTCCT TTAATTTCAA GGAATTATAG AACAAAAAAT GTTCTTTATA AAAATTAAGA
AGGAACAAGG GATTCATTCC TACTATTCTG TTCTTGGTCA TTATTTTCCT CTTCATTCAT
ATTGTTTCTT TAATTGTTAC CAATTAGAAC TTTAACGAAT AAATAGTTAA TTCGTATTAT
GAGATTTACA CAATTCTTAT TCACTCAATT TGGAGTTTTA AAGATTTTTT AAAAGATTTA
TGGTGGGAAC CTTCTTCTTT TCTTATTTAT CATGATGATG ATAACCTTCC CAGCAGAATT
ATTCTTAGAA CTTTTTTTCA CATTTAGGTA TCCATGCCTA AGTAAGGCTT AGTTAAAGAT
GTTTTATAAA CTTTGATCAA AATATTCATT CAATTAATTT GAGCTTCAAC TATAAATTGT
TGTATGCATT CGTTTTAGCC TGTAAGATAT CAGACATTCA CGTTTCGATA AACAAGTATA
TAAATAATAT GAATATTGTA CATTCATTTT ATTCGGTTCA TCAACCAAAA AAAATAAAAA
TAAATATTCG TATTCATCTA TGCTTTGGCA TGGTCCGTTC TTTTTTCTTG ATTGGCTCGT
TACCATTCAA AAATATATAC CTTAGCAAAC CCATTTTTAG ACATTCCAGT TGATCTACAT
TAGATTGAAC GGTATTCCTC CTACGTAGTA AGAACGTTTT CTATTTTTCT TTGTTTCAGT
CATACAACAC AACTATATAT ACACAGCAAC CCCATCTCCT CTCCAATCAT CACAATCTCT
              *    *    *    *    *    *    *
AACGTTAAAC CCTAAGACAA ACTAAAAGAG AGCTACGTAC AAGGAGACAG AGAGAAGA
                  *           *
ATG GGT CGC CAA AAC GCT GTC GTA GTT TTT GGC CTT GTG TTC TTG GCC
Met Gly Arg Gln Asn Ala Val Val Val Phe Gly Leu Val Phe Leu Ala
 1           5                    10                      15
 *
ATC CTT GGC CTC GCC GCA GCT GCC TCC TCT CCG TCT CCT TCA GCG TCA
Ile Leu Gly Leu Ala Ala Ala Ala Ser Ser Pro Ser Pro Ser Ala Ser
             20         *   *   *   25  * *    *       30
 *
CCC TCC AAA GCT CCG GCT GCT ACC GTA ACC GAT GTC GAA GCT CCA GTG
Pro Ser Lys Ala Pro Ala Als Thr Val Thr Asp Val Glu Ala Pro Val
         35                  40                  45
 * *                                                         *
AGC GAG GAC ACC ATT GGA ACC ACC GAT GAC GAT GCA GCT GCT TCT CCA
Ser Glu Asp Thr Ile Gly Thr Thr Asp Asp Asp Ala Ala Ala Ser Pro
         50              55                  60
          *
GGT GAT GGT GAC GTA GCT GTG GCT GGT CCT CTA GGA AGT GAC TCC TCC
Gly Asp Gly Asp Val Ala Val Ala Gly Pro Leu Gly Ser Asp Ser Ser
65                   70              75                      80
     *                   * * *    * *    *
TAC GGT AGT AAT GGA CCT TCA CCT TCT ACT GAT GCT GCT GAC AGC GGC
Tyr Gly Ser Asn Gly Pro Ser Pro Ser Thr Asp Ala Ala Asp Ser Gly
                 85                  90
     * *         *                   * *    *
GCG CCT GCT CTT GGC GTC TCT GCG GTC TTC GTT GGT GTT GCA TCC ATC
Ala Pro Ala Leu Gly Val Ser Ala Val Phe Val Gly Val Ala Ser Ile
             100             *           105            110
 *                  *                        *       * *    *
GCC GGT TCT TTC TTG TTT CTC TGAGGTGTGT ATTATCATGA GAAGATTATT
Ala Gly Ser Phe Leu Phe Leu
             115
A─────────────────────────────────────────────────────────────A
```

Figure 1A

```
A─────────────────────────────────────────────────────────────────A
     *              *         *         *            *    *        * *
CTGACTGAAG ACTATTAATA TGTATGGATG ATTGTGATGG TCGTGTTGTA ATATGTTTCT
  **  *          *       *   **           ***
CCTTTATTGT GAGAAACGAT GTTTTGCTAA TAAAACTGAA AAAAAAAACG AAAATTTCCT
CTAGCCAAGG ATAAAATGCC GGAATTGCGG ATTAAATAGT ACTATTCAAT CCTTTCATGT
TTTCGAGATA CAAAAATACA TATTAATCAG GTAGAGCCGT AGAAGTCCGT AACCACTGGA
TACAATCTTT TTCGTAGTAA GAAAGAAAGT ACAATCTTAT TCTAAATGCA TGTGTTTGAT
AGATTATGGA ACGGTGAGAA GGGCATTGAT TATGGGAGTT ATGATCGAAG ATACACACGA
TACCATCTTT TTAGGTATAG CTTCTTCTTC TATAAA
```

Figure 1B

```
AAAAGCGAGA AGAAGAAGTC TGGAAGATTT GAGAGCTTAA AGTGGTCGAG TGTAAAACCC
TAACTCGCTG TTGATGGCAG AATCGTAAAT CGGAATTGAT TCATGGGCCT AACAAGACGT
TTGGGCTTAT GGGTTTAAAG CCCATCTGAT ATAAGATGAA TAGAATGTTC ATGGCAATAC
TATCATAATT TGGTTCTTTA ATAAGACACT CGTTAATACG ACGACGATTT GAAGTTGAAC
GAATGTTTTC ATATTCATTC GCATGTTCAC CAATCAAAAT CTATATCTGA ACAAGTCCAT
TTTTAGGTAC TCCAGTAGAT TTACATTGGA TTGTAAGGTA ATCCTACATC TTAGTTCACG
TTTTCTATTT TTGGTCTTGT CACTAAACAC AACTATATAT ACATATCAAA CTCATCTTCG
GAAATCATCA CAATCAATAA ACCTCAAACC CTAAAATAAA TTAAACGAGT TCTACGTAAG
AAGGAGAGAG AGAAGA ATG GGT CGC CAA AAC ATT GTC GTC GTC GTT GCC
               Met Gly Arg Gln Asn Ile Val Val Val Val Ala
                1            3                          10
CTC GTC TTC ATC CGG ATC ATT GGC CTT GCC GCA GCT GCC TCC TCT CCA
Leu Val Phe Ile Arg Ile Ile Gly Leu Ala Ala Ala Ala Ser Ser Pro
            15              20                      25
TCT CCT TCA GCG TCT CCC TCC AAA GCT CCA GCT GCC TCC AAA ACC GAT
Ser Pro Ser Ala Ser Pro Ser Lys Ala Pro Ala Ala Ser Lys Thr Asp
        30              35                      40
CAT GTC GAG GCT CCA GTC ACC GAT GAC CAA ATC GGA ACC ACC GAT GAC
His Val Glu Ala Pro Val Thr Asp Asp Gln Ile Gly Thr Thr Asp Asp
    45              50                      55
GAT GCA GCT CCT ACT CCT GGT GAC GGT GAC GTT GCA GTG GCT GGT CCT
Asp Ala Ala Pro Thr Pro Gly Asp Gly Asp Val Ala Val Ala Gly Pro
 60              65                      70                   75
CTA GGA AGT GAC TCC TCG TAC GAC AAT GCC CCT ACA GGC TCT GCT GAT
Leu Gly Ser Asp Ser Ser Tyr Asp Asn Ala Ala Thr Gly Ser Ala Asp
                80                      85                   90
TCT GCC AAA AGC GGT GCG GCA GCT CTT GGC GTC TCT GCG GTC GTC GTT
Ser Ala Lys Ser Gly Ala Ala Ala Leu Gly Val Ser Ala Val Val Val
            95                      100                  105
GGT GTT ACA TCA TTG CTG GTT CTT TCT TGT TAC TCA AGT TGG GCA TTG
Gly Val Thr Ser Leu Leu Val Leu Ser Cys Tyr Ser Ser Trp Ala Leu
        110                 115                  120
TTT TAT GAT AAG AAG GTT ATT TTA AAC GAA GAT TAT TAT ATG
Phe Tyr Asp Lys Lys Val Ile Leu Asn Glu Asp Tyr Tyr Met
    125                 130                  135
TAAGGATGAT TGTGATGATC CGTTGACCTG CAGGTCGACC CAGATCCGCC TACCTTTCAC
GAGTTGCGCA GTTTGTCTGC AAGACTCTAT GAGAAGCTGA TAAGAGATAA GTTGCTCAA
CATCTTCTCG GCATAAGTC CGGACACCAT GGCATCACAG TATCGAGATG ACAGAGGCAG
GGAGTGGGAC AAAATTGAAA TCAAATGATC GATTTTATTT TGGCT
```

Figure 11B

DEVELOPMENTAL REGULATION IN ANTHER TISSUE OF PLANTS

FIELD OF THE INVENTION

The present invention relates generally to the use of genetic engineering to induce developmental regulation in anther tissue of plants, and more particularly to induce nuclear male sterility, and to genetic sequences useful for same.

Nucleotide and amino acid sequences are referred to herein by sequence identity numbers (SEQ ID NOs) which are defined after the bibliography. A general summary of the SEQ ID NOs is provided before the examples.

Throughout this specification and the claims which follow, unless the context requires otherwise, the word "comprise", or variations such as "comprises" or "comprising", will be understood to imply the inclusion of a stated element or integer or group of elements or integers but not the exclusion of any other element or integer or group of elements or integers.

Anther-specific genes are those genes that are expressed exclusively in the male reproductive tissues, rather than "house-keeping" genes which are active in all plant cells. Anther-specific genes play an important role in pollen development and, hence, in the control of seed production.

Differentiation and development of the male gametophyte of angiosperms, the pollen grain, depends partly upon transcription of the haploid genome following meiosis (Mascarenhas, 1988). The study of these coordinated events at the molecular level has been considered important in order to understand the developmentally specific regulation and functions of pollen-expressed genes. In this regard, Theerakulpisut et al (1991) studied gene expression in pollen of *Brassica campestris*. By differential screening of a mature *B. campestris* pollen cDNA library, an anther-specific clone, designated Bcp1, was isolated.

In work leading up to the present invention, the inventors undertook a detailed investigation of Bcp1 expression with the aim of isolating a genomic clone and to sub-clone and characterise the 5' upstream regulatory regions of the genomic clone. It has been surprisingly discovered that the genomic clone of Bcp1, i.e. Bgp1, is tissue and developmentally specific thereby providing a means to enable tissue and developmental regulation in plants and in particular to produce nuclear male sterile plants. It has further been discovered that the Bgp1 gene from *B. campestris* represents a family of homologous genes from a diverse range of plants. By way of shorthand notation, a genomic clone is referred to herein by the genus and/or species of the plant from which it is isolated followed by the term "Bgp1". A cDNA clone is referred to in similar fashion except using the term "Bcp1".

SUMMARY OF THE INVENTION

Accordingly, one aspect of the present invention contemplates a genomic DNA isolate comprising:

(i) all or part of a gene or related genetic sequence preferentially expressed in anther tissue of a plant and substantially not expressed in non-anther tissue; and (ii) an open reading frame having a nucleotide sequence as set forth in SEQ ID NO. 1:

```
ATG GGT CGC CAA AAC GCT GTC GTA GTT TTT GGC CTT GTG TTC TTG CCC

ATC CTT GGC CTC GCC GCA GCT GCC TCC TCT CCG TCT CCT TCA GCG TCA

CCC TCC AAA GCT CCG GCT GCT ACC GTA ACC GAT GTC GAA GCT CCA GTG

AGC GAG GAC ACC ATT GGA ACC ACC GAT GAC GAT GCA GCT GCT TCT CCA

GGT GAT GGT GAC GTA GCT GTG GCT CGT CCT CTA GGA AGT GAC TCC TCC

TAC GCT AGT AAT GGA CCT TCA CCT TCT ACT GAT GCT GCT GAC AGC GGC

GCC CCT GCT CTT GGC GTC TCT GCG GTC TTC GTT GGT GTT GCA TCC ATC

GCC GGT TCT TTC TTG TTT CTC
``` or having at least 20% similarity to all or part thereof.

The deduced amino acid sequence to the open reading frame defined in SEQ ID NO. 1 is shown in SEQ ID NO. 2.

The expression "gene or related genetic sequence" is used in is broadest sense and includes any contiguous series of nucleotides constituting an open reading frame. Generally, an open reading frame comprises at least 48 contiguous nucleotides arranged into triplets without interuption by a stop codon.

A nucleotide sequence having at least 20% similarity to all or a portion of SEQ ID NO. 1 is referred to herein as a "homologous gene". Preferably, there is at least 20% similarity to the entire SEQ ID NO. 1 sequence. Even :more preferably, there is at least 30% similarity, still more preferably at least 45% similarity, even still more preferably at least 55–60% similarity, yet even still more preferably at least 75–95% similarity to all or part of SEQ ID NO. 1. A "part" in this context is a contiguous series of at least 20 nucleotides in SEQ ID NO. 1.

Preferably, the genomic DNA isolate is a dicotyledonous plant such as tomato, corn, rice, wheat, raddish, tobacco and oil seed rapes. Particularly preferred plants are Brassica species, Arabidopsis species and Nicotiana species.

In a most preferred embodiment, the plant is *Brassica campestris* and the genomic DNA isolate has an open reading frame with a sequence as set forth in SEQ ID NO. 1. A preferred homologous gene having at least 20% nucleotide similarity to SEQ ID NO. 1 is from *Arabidopsis thaliana* comprising an open reading frame with a nucleotide sequence as set forth in SEQ ID NO. 3:

```
ATG GGT CGC CAA AAC ATT GTC GTC GTG GTT GCC CTC GTC TTC ATC CGG

ATC ATT GGC CTT GCC GCA GCT GCC TCC TCT CCA TCT CCT TCA GCG TCT

CCC TCC AAA GCT CCA GCT GCC TCC AAA ACC GAT CAT GTC GAG GCT CCA

GTC ACC GAT GAC CAA ATC GGA ACC ACC GAT GAC GAT GCA GCT CCT ACT

CCT GGT GAC GGT GAC GTT GCA GTG GCT GGT CCT CTA GGA AGT GAC TCC

TCG TAC GAC AAT GCC GCT ACA GGC TCT GCT GAT TCT GCC AAA AGC GGT

GCG GCA GCT CTT GGC GTC TCT GCG GTC GTC CTT GGT GTT ACA TCA TTG

CTG GTT CTT TCT TGT TAC TCA AGT TGG GCA TTG TTT TAT GAT AAG AAG

GTT ATT TTA AAC GAA GAT TAT TAT ATG
```

The deduced amino acid sequence of SEQ ID NO. 3 is defined in SEQ ID NO. 4.

Another aspect of the present invention provides a genomic DNA isolate as defined above and further comprising a promoter region 5' to the open reading frame, wherein said promoter region:

(i) is capable of directing expression in taptum and/or pollen tissue; and
(ii) comprises a nucleotide sequence as set forth in, SEQ ID NO. 5:

```
TATCATTCCT TTAATTTCAA GGAATTATAG AACAAAAAAT GTTCTTTATA AAAATTAAGA

AGGAACAAGG GATTCATTCC TACTATTCTG TTCTTGGTCA TTATTTTCCT CTTCATTCAT

ATTGTTTCTT TAATTGTTAC CAATTAGAAC TTTAACGAAT AAATAGTTAA TTCGTATTAT

GAGATTTACA CAATTCTTAT TCACTCAATT TGGAGTTTTA AAGATTTTTT AAAAGATTTA

TGGTGGGAAC CTTCTTCTTT TCTTATTTAT CATGATGATG ATAACCTTCC CAGCAGAATT

ATTCTTAGAA CTTTTTTTCA CATTTAGGTA TCCATGCCTA AGTAAGGCTT AGTTAAAGAT

GTTTTATAAA CTTTGATCAA AATATTCATT CAATTAATTT GAGCTTCAAC TATAAATTGT

TGTATGCATT CGTTTTAGCC TGTAAGATAT CAGACATTCA CGTTTCGATA AACAAGTATA

TAAATAATAT GAATATTGTA CATTCATTTT ATTCGGTTCA TCAACCAAAA AAAATAAAAA

TAAATATTCG TATTCATCTA TGCTTTGGCA TGGTCCGTTC TTTTTTCTTG ATTGGCTCGT

TACCATTCAA AAATATATAC CTTAGCAAAC CCATTTTTAG ACATTCCAGT TGATCTACAT

TAGATTGAAC GGTATTCCTC CTACGTAGTA AGAACGTTTT CTATTTTTCT TTGTTTCAGT

CATACAACAC AACTATATAT ACACAGCAAC CCCATCTCCT CTCCAATCAT CACAATCTCT

AACGTTAAAC CCTAAGACAA ACTAAAAGAG AGCTACGTAC AAGGAGACAG AGAGAAGA
``` or having at least 20% similarity to all or part thereof.

Preferred promoters comprise the promoter defined in SEQ ID NO. 5 and the promoter defined in SEQ D NO. 6 which has the following nucleotide sequence:

```
AAAAGCGAGA AGAAGAAGTC TGGAAGATTT GAGAGCTTAA AGTGGTCGAG TCTAAAACCC

TAACTCGCTG TTGATGGCAG AATCGTAAAT CGGAATTGAT TCATGGGCCT AACAAGACGT

TTGGGCTTAT GGGTTTAAAG CCCATCTGAT ATAAGATGAA TAGAATGTTC ATGGCAATAC

TATCATAATT TGGTTCTTTA ATAAGCACAT CCTTAATACG ACGACGATTT GAAGTTGAAC

GAATCTTTTC ATATTCATTC GCATGTTCAC CAATCAAAAT CTATATCTGA ACAAGTCCAT

TTTTAGGTAC TCCAGTAGAT TTACATTGGA TTGTAAGGTA ATCCTACATC TTAGTTCACG

TTTTCTATTT TTGGTCTTGT CACTAAACAC AACTATATAT ACATATCAAA CTCATCTTCG
```

-continued

```
GAAATCATCA CAATCAATAA ACCTCAAACC CTAAAATAAA TTAAACGAGT TCTACGTAAG

AAGGAGAGAG AGAAGA
```

Yet another aspect of the present invention relates to a genomic DNA isolate comprising:
(i) all or part of a gene or related genetic sequence preferentially expressed in anther tissue of a plant and substantially not expressed in non-anther tissue;
(ii) a promoter region capable of directing expression in tapetum and/or pollen tissue;
(iii) a nucleotide sequence substantially as set forth in SEQ ID NO. 7:

or having at least 20% similarity to all or part thereof.

In a preferred embodiment, the above genomic DNA isolate further comprises:
(iv) a nucleotide sequence which is capable of hybridising under low stringency conditions to all or part of a nucleotide sequence substantially complementary to SEQ ID NO. 7.

Most preferred genomic DNA isolates comprise SEQ ID NO. 7 and SEQ ID NO. 8, the latter which has the following nucleotide sequence:

```
TATCATTCCT TTAATTTCAA GCAATTATAG AACAAAAAAT GTTCTTTATA AAAATTAAGA

AGGAACAAGG GATTCATTCC TACTATTCTG TTCTTGGTCA TTATTTTCCT CTTCATTCAT

ATTGTTTCTT TAATTGTTAC CAATTAGAAC TTTAACGAAT AAATAGTTAA TTCGTATTAT

GAGATTTACA CAATTCTTAT TCACTCAATT TGGAGTTTTA AAGATTTTTT AAAAGATTTA

TGGTGGGAAC CTTCTTCTTT TCTTATTTAT CATGATGATG ATAACCTTCC CAGCAGAATT

ATTCTTAGAA CTTTTTTTCA CATTTAGGTA TCCATGCCTA AGTAAGGCTT AGTTAAAGAT

GTTTTATAAA CTTTGATCAA AATATTCATT CAATTAATTT GAGCTTCAAC TATAAATTGT

TGTATGCATT CGTTTTAGCC TGTAAGATAT CAGACATTCA CGTTTCGATA AACAAGTATA

TAAATAATAT GAATATTGTA CATTCATTTT ATTCGGTTCA TCAACCAAAA AAAATAAAAA

TAAATATTCG TATTCATCTA TGCTTTGGCA TGGTCCGTTC TTTTTTCTTG ATTGGCTCGT

TACCATTCAA AAATATATAC CTTAGCAAAC CCATTTTTAG ACATTCCAGT TGATCTACAT

TAGATTGAAC GGTATTCCTC CTACGTAGTA AGAACGTTTT CTATTTTTCT TTGTTTCAGT

CATACAACAC AACTATATAT ACACAGCAAC CCCATCTCCT CTCCAATCAT CACAATCTCT

AACGTTAAAC CCTAAGACAA ACTAAAAGAG AGCTACGTAC AAGGAGACAG AGAGAAGAAT

GGGTCGCCAA AACGCTGTCG TAGTTTTTGG CCTTGTGTTC TTGGCCATCC TTGGCCTCGC

CGCAGCTGCC TCCTCTCCGT CTCCTTCAGC GTCACCCTCC AAAGCTCCGG CTGCTACCGT

AACCGATGTC GAAGCTCCAG TGAGCGAGGA CACCATTGGA ACCACCGATG ACGATGCAGC

TGCTTCTCCA GGTGATGGTG ACGTAGCTGT GGCTGGTCCT CTAGGAAGTG ACTCCTCCTA

CGGTAGTAAT GGACCTTCAC CTTCTACTGA TGCTGCTGAC AGCGGCGCGC CTGCTCTTGG

CGTCTCTGCG GTCTTCGTTG GTGTTGCATC CATCGCCGGT TCTTTCTTGT TTCTCTGAGG

TGTGTATTAT CATGAGAAGA TTATTCTGAC TGAAGACTAT TAATATGTAT GGATGATTGT

GATGGTCGTG TTGTAATATG TTTCTCCTTT ATTGTGAGAA ACGATGTTTT GCTAATAAAA

CTGAAAAAAA AAACGAAAAT TTCCTCTAGC CAAGGATAAA ATGCCGGAAT TGCGGATTAA

ATAGTACTAT TCAATCCTTT CATGTTTTCG AGATACAAAA ATACATATTA ATCAGGTAGA

GCCGTAGAAG TCCGTAACCA CTGGATACAA TCTTTTTCGT AGTAAGAAAG AAAGTACAAT

CTTATTCTAA ATGCATGTGT TTGATAGATT ATGGAACGGT GAGAAGGGCA TTGATTATGG

GAGTTATGAT CGAAGATACA CACGATACCA TCTTTTTAGG TATAGCTTCT TCTTCTATAA
```

A

```
AAAAGCGAGA AGAAGAAGTC TGGAAGATTT GAGAGCTTAA AGTGGTCGAG TGTAAAACCC

TAACTCGCTG TTGATGGCAG AATCGTAAAT CGGAATTGAT TCATGGGCCT AACAAGACGT

TTGGGCTTAT GGGTTTAAAG CCCATCTGAT ATAAGATGAA TAGAATGTTC ATGGCAATAC

TATCATAATT TGGTTCTTTA ATAAGACACT CGTTAATACG ACGACGATTT GAAGTTGAAC

GAATGTTTTC ATATTCATTC GCATGTTCAC CAATCAAAAT CTATATCTGA ACAAGTCCAT

TTTTAGGTAC TCCAGTAGAT TTACATTGGA TTGTAAGGTA ATCCTACATC TTAGTTCACG

TTTTCTATTT TTGGTCTTGT CACTAAACAC AACTATATAT ACATATCAAA CTCATCTTCG

GAAATCATCA CAATCAATAA ACCTCAAACC CTAAAATAAA TTAAACGAGT TCTACGTAAG

AAGGAGAGAG AGAAGAATGG GTCGCCAAAA CATTGTCGTC GTGGTTGCCC TCGTCTTCAT

CCGGATCATT GGCCTTGCCG CAGCTGCCTC CTCTCCATCT CCTTCAGCGT CTCCCTCCAA

AGCTCCAGCT GCCTCCAAAA CCGATCATGT CGAGGCTCCA GTCACCGATG ACCAAATCGG

AACCACCGAT GACGATGCAG CTCCTACTCC TGGTGACGGT GACGTTGCAG TGGCTGGTCC

TCTAGGAAGT GACTCCTCGT ACGACAATGC CGCTACAGGC TCTGCTGATT CTGCCAAAAG

CGGTGCGGCA GCTCTTGGCG TCTCTGCGGT CGTCGTTGGT GTTACATCAT TGCTGGTTCT

TTCTTGTTAC TCAAGTTGGG CATTGTTTTA TGATAAGAAG GTTATTTTAA ACGAAGATTA

TTATATGTAA GGATGATTGT GATGATCCGT TGACCTGCAG GTCGACCCAG ATCCGCCTAC

CTTTCACGAG TTGCGCAGTT TGTCTGCAAG ACTCTATGAG AAGCTGATAA GAGATAAGTT

TGCTCAACAT CTTCTCGGGC ATAAGTCCGG ACACCATGGC ATCACAGTAT CGAGATGACA

GAGGCAGGGA GTGGGACAAA ATTGAAATCA AATGATCGAT TTTATTTTGG CT
```

Still yet another aspect of the present invention contemplates an isolated nucleic acid molecule which is capable of hybridising under low stringency conditions to the genomic DNA isolates defined above. Preferred nucleic acid molecules comprise a complementary strand of all or part of SEQ ID NO. 1 or SEQ ID NO. 3. A "part" in this context includes an oligonucleotide.

A further aspect of the present invention provides a genetic construct comprising:
(i) a promoter region capable of directing expression of a nucleotide sequence when operably linked downstream thereof in tapetum and/or pollen tissue; and
(ii) said promoter being capable of hybridising under low stringency conditions to a complementary strand of SEQ ID NO. 5.

For the purposes of defining the level of stringency, reference can conveniently be made to Sambrook et al., Supra at pp 387–389 which is herein incorporated by reference where the washing step at paragraph 11 is considered high stringency. A low stringency is defined herein as being in 0.1–0.5% w/v SDS at 37–45° C. for 2–3 hours. Depending on the source and concentration of nucleic acid involved in the hybridisation, alternative conditions of stringency may be employed such as medium stringent conditions which are considered herein to be 0.25%–0.5% w/v SDS at ≧45° C. for 2–3 hours or high stringent conditions as disclosed by Sambrook et al., Supra.

In a further related embodiment, there is provided a nucleic acid isolate having a sequence of nucleotides comprising or a complementary sequence of nucleotides comprising SEQ ID NO. 5 or a promoter functional derivative, fragment, part, homologue or analogue thereof. The latter functional derivative and like molecules comprise at least 20% nucleotide sequence similarity to SEQ ID NO. 5. An example of a promoter having at least 20% nucleotide similarity to SEQ ID NO. 5 is the promoter from *A. thaliana* Bgp1 having the sequence set forth in SEQ ID NO. 6.

In accordance with these and other aspects of the present invention, the term "promoter" is used in its most general sense and refers to any nucleotide sequence which binds RNA polymerase and directs same to a transcriptional start site whereupon a gene or other nucleotide sequence downstream of said promoter is transcribed. A nucleotide sequence "downstream" of the promoter is also said to be "relative" the promoter.

The term "genetic construct" is used in its most broadest sense to include an isolated nucleic acid molecule comprising a sequence of nucleotides.

Preferably, the promoter is from a Brassica species such as *B. compestris* or from an Arabidopsis species such as *A. thaliana*. Preferably, the genetic construct is transformable and operable in dicotyledon plants and in particular a Brassica species, Arabidopsis species or a Nicotiana species.

The genetic construct may be conveniently engineered so as to place an endonuclease restriction site in a region 3' of the promoter to thereby readily enable the insertion of nucleotide sequences downstream of the promoter for their transcription. Generally, the inserted restriction site is unique to the genetic construct or may be represented twice but separated by a length of nucleic acid to be deleted upon restriction digestion of the genetic construct and followed by insertion of the required nucleotide sequence to be transcribed.

The genetic construct of the present invention may comprise solely the promoter and optionally a nucleotide sequence downstream thereof or, alternatively, may comprise additional nucleotide sequences constituting promoter regulatory region(s), transcribed sequence regulatory regions, a marker (eg. antibiotic resistance, chemical compound resistance or enzyme), autonomous replication region and/or genome integration sequence. The promoter may be the naturally occurring promoter or may be an active fragment or part thereof or a derivative, analogue or homologue of the promoter.

By "derivative" is meant to include any single or multiple nucleotide deletion, insertion and/or substitution to the promoter nucleotide sequence, provided said derivative is still active in tapetum and/or pollen tissue. Manipulation of the nucleotide sequence at known predetermined sites or random mutagenesis are conveniently accomplished by any number of techniques including M13, transposon and/or oligonucleotide mutagenesis. Various techniques are described by Maniatis et al (1989).

Homologues and analogues of the promoter include promoters having a nucleotide sequence having at least 20%, preferably at least 30% similarity, more preferably at least 45% similarity, still more preferably at least 55–60% similarity and even more preferably at least 75–95% similarity to the first mentioned promoter and which function in anther tissue.

Most preferred promoters comprise the sequence SEQ ID NO. 5 or SEQ ID NO. 6.

The promoter of the present invention is tissue specific for anther tissue. More particularly, the promoter is specific for tapetum and/or pollen tissue. However, this is not intended to exclude genetic constructs based on the promoter of the present invention but modified to be capable of expression in non-anther tissues.

The nucleotide sequence down stream of the promoter might give rise to antisense RNA or may encode specific traits such as a "lethal gene" or a "Miller gene" to specifically render a pollen grain infertile or incapable of maturation. The nucleotide sequence may also encode a trait, for example, which renders the pollen grain more resistant to predator or pathogen attack. In one particular embodiment, the nucleotide sequence downstream of the promoter is a ribozyme capable of targetting a mRNA transcript corresponding to SEQ ID NO. 1 or SEQ ID NO. 3 or a homologous genetic sequence thereof.

According to this latter embodiment, there is provided a ribozyme which comprises a hybridising region and a catalytic region wherein the hybridising region is capable of hybridising to at least part of a target mRNA sequence transcribed from a genomic Bgp1 gene as hereinbefore defined wherein the catalytic region is capable of cleaving said target mRNA thereby substantially down regulating expression of said genomic DNA isolate. A ribozyme according to this aspect of the invention may also be a polyribozyme.

Methods for the construction of ribozyme are conveniently disclosed in Haseloff and Gerlach (1988) and in International Patent Application No. WO89/05852. Preferably, the ribozyme is under the control of a Bgp1 promoter as hereinbefore described.

The present invention further extends to a hybrid genetic sequence comprising a ribozyme as hereinbefore described fused, linked or otherwise chemically bonded to one or more sequence of nucleotides which is/are substantially antisense to all or part of SEQ ID NO. 1 or a homologous sequence (e.g. antisense to all or part of SEQ ID NO. 3).

The antisense sequence may flank both sides of a ribozyme or may be located to one end of said ribozyme. Reference to a ribozyme in this context includes reference to a polyribozyme. A "substantially antisense" molecule is a molecule capable of hybridising under physiological conditions to the reference sequence (e.g. SEQ ID NO. 1 or SEQ ID NO. 3) to a sufficient extent to reduce translation of said target sequence into functional protein or which results in male sterility.

The present invention is particularly exemplified using the promoter isolated from a genomic clone of Bcp1, the genomic clone being designated herein "Bgp1", from Brassica species or non-Brassica species with similar acting promoters. Such other promoters are referred to herein as "homologous promoters" and include the promoter from the homologous gene *A. thaliana* Bgp1 defined by SEQ ID NO. 6. Most of the Bgp1 promoter is required for pollen expression and in particular nucleotide regions −580 to −767, −322 to −580 and −116 to −168 whereas the nucleotide region up to −116 is only required for tapetum expression.

According to a preferred embodiment, the present invention provides an isolated nucleic acid molecule carrying a promoter capable of directing expression in tapetum and pollen tissue and comprising the following nucleotide sequence identified as SEQ ID NO. 5, including functional derivatives or homologue having at least 20% nucleotide similarity to all or a part thereof and/or which are capable of hybridising to a complementary strand thereof under at least low stringency conditions.

According to another embodiment, there is provided an isolated nucleic acid molecule carrying a promoter capable of directing expression in pollen tissue but not tapetum, said nucleic acid molecule comprising the following nucleotide sequence identified as SEQ ID NO. 9:

```
TATCATTCCT TTAATTTCAA GGAATTATAG AACAAAAAAT GTTCTTTATA AAAATTAAGA

AGGAACAAGG GATTCATTCC TACTATTCTG TTCTTGGTCA TTATTTTCCT CTTCATTCAT

ATTGTTTCTT TAATTGTTAC CAATTAGAAC TTTAACGAAT AAATAGTTAA TTCGTATTAT

GAGATTTACA CAATTCTTAT TCACTCAATT TGGAGTTTTA AAGATTTTTT AAAAGATTTA

TGGTGGGAAC CTTCTTCTTT TCTTATTTAT CATGATGATG ATAACCTTCC CAGCAGAATT

ATTCTTAGAA CTTTTTTTCA CATTTAGGTA TCCATGCCTA AGTAAGGCTT AGTTAAAGAT

GTTTTATAAA CTTTGATCAA AATATTCATT CAATTAATTT GAGCTTCAAC TATAAATTGT

TGTATGCATT CGTTTTAGCC TGTAAGATAT CAGACATTCA CGTTTCGATA AACAAGTATA

TAAATAATAT GAATATTGTA CATTCATTTT ATTCGGTTCA TCAACCAAAA AAAATAAAAA
```

-continued

```
TAAATATTCG TATTCATCTA TGCTTTGGCA TGGTCCGTTC TTTTTTCTTG ATTGGCTCGT

TACCATTCAA AAATATATAC CTTAGCAAAC CCATTTTTAG ACATTCCAGT TG
``` including functional derivatives or homologues having at least 20% nucleotide similarity to all or a part thereof and/or which are capable of hybridising to a complementary strand thereof under at least low stringency conditions.

A particularly important homologue is SEQ ID NO. 6 from A. thaliana.

Preferably, the nucleotide sequence of SEQ ID NO. 5, SEQ ID NO. 9 or SEQ ID NO. 6 is modified by the introduction of a restriction endonuclease cleavage site to facilitate the insertion of an operably linked second nucleotide sequence downstream of the promoter.

Preferably, the nucleotide sequence of the present invention form part of a vector.

The identification of a tissue and developmentally dependent promoter enables the production of genetic constructs which can be used to generate transgenic plants having certain traits expressed or down regulated. For example, the function of the Bgp1 gene can be conveniently disrupted using antisense RNA or a ribozyme. Conveniently, the cDNA clone Bcp1 is inserted in the reverse orientation relative the Bgp1 promoter. This construct, when introduced into a suitable host, produces antisense RNA which disrupts expression of the Bgp1 gene. Although not intending to limit the present invention to any one theory of mode of action, it is possible the antisense RNA forms a duplex with Bgp1 RNA to thereby prevent its translation. Transgenic plants carrying the particular construct are generally male sterile but female fertile.

According to this aspect of the present invention there is provided an antisense construct:

(i) which comprises a nucleic acid molecule comprising at least eight contiguous nucleotides;

(ii) which is capable of hybridising under physiological conditions to all or part of SEQ ID NO. 1 or a homologous.-sequence thereof; and (iii) which, in use, is capable of down regulating expression of a plant Bgp1 gene.

In this context, a "homologous" sequence comprises a nucleotide sequence having at least 20% similarity to all or part of SEQ ID NO. 1 and which is a Bgp1 gene.

Preferably, the antisense construct is at least 20 nucleotides long. More preferably, the antisense construct is at least 50–100 nucleotides long. Even more preferably, the antisense construct is all or part of a plant Bcp1 or Bgp1 in reverse orientation relative a promoter.

The term "down regulates" or similar expressions such as "down regulating" means a reduction in the amount of full length Bgp1 mRNA as determined by hybridisation or extent of translation into a Bgp1 product or, most conveniently, generation of substantially male sterile plants.

Yet another aspect of the present invention contemplates a method for generating male sterile plants, said method comprising transforming a cell or group of cells of said plant with a genetic construct capable of directing expression of a nucleotide sequence having a deleterious effect on tapetum and/or pollen tissue, regenerating a transgenic plant from said transformed cells and growing and/or maintaining said transgenic plant under conditions to thereby having a deleterious effect on said tapetum and/or pollen tissue resulting in said plant being substantially male sterile.

In an alternative embodiment, there is provided a method for generating male sterile plants, said method comprising introducing into a cell or group of cells of said plant, a genetic construct comprising all or part of a Bgp1, said Bgp1 having a nucleotide sequence substantially similar to an endogenous Bgp1 of the plant and then regenerating a plant from said cells. This method is term "co-suppression". The introduced Bgp1 may be with or without a promoter. By "substantially" similar is meant an exogenous Bgp1 comprising 85–100% nucleotide sequence similarity to an endogenous Bgp1.

Still yet another aspect of the present invention provides a transgenic male sterile plants such as those made by the above method.

The present invention is further described by the following non-limiting Figures and Examples:

BRIEF DESCRIPTION OF THE DRAWINGS

FIGS. 1A and 1B, when joined at match line A—A, show the nucleotide sequence of Bgp1 (SEQ ID NO. 7) having the coding region along with 5' flanking region and 3' flanking region; nucleotide numbering is relative to the start of the transcription at position number 1. The amino acid sequence of the putative Bgp1 protein is shown (SEQ ID NO. 2). The TATA box and the ATG translational start codon are underlined. Nucleotides which differ between the sequences of Bgp1 and Bcp1 are indicated by asterisks above the sequence.

FIG. 10A is an RNA gel bot analysis showing the differential expression in vegetative and reproductive tissues. The transcripts of approximately 700 bp were detected in flowers, but not in the vegetative tissues tested. FIGS. 10B and 10C show in situ hybridisation of flower sections with biotin-labelled antisense Bgp1-specific riboprobes. FIGS. 10D and 10E show in situ hybridizations of flower sections with biotin-labeled sense Bgp1-specific riboprobes. Flowers at two different developmental stages were used. RNA-RNA hybridisation signal was detected as bright regions on the sections. In immature flowers, an intensive hybridisation signal is present in the microspores (Mi) and the intact tapetal cells (Tc). In mature flowers, a very strong signal is present in pollen (Po) whereas only low level of signal is present in the remnants of tapetal cells (Tc) due to self-degeneration.

Total RNAs were isolated and used (15 μg/lane) for, the gel blot as described (Maniatis et al., 1989). The blot was hybridised with a $^{32}$P-labelled probe derived from Brassica Bcp1 cDNA clone. Flowers at relevant stages were collected, fixed and embedded in LR white resin for in situ hybridisation essentially as described (Theerakulpisut et al., 1991). Biotin-labelled sense and antisense riboprobes were generated by in vitro transcription from the Bcp1 cDNA clone. Hybridisation signal was detected using colloidal gold (15 nm) conjugated.,rabbit anti-biotin antibody (1:15 dilution), followed by silver enhancement. Sections were viewed under dark field microscopy.

Figure 11A:
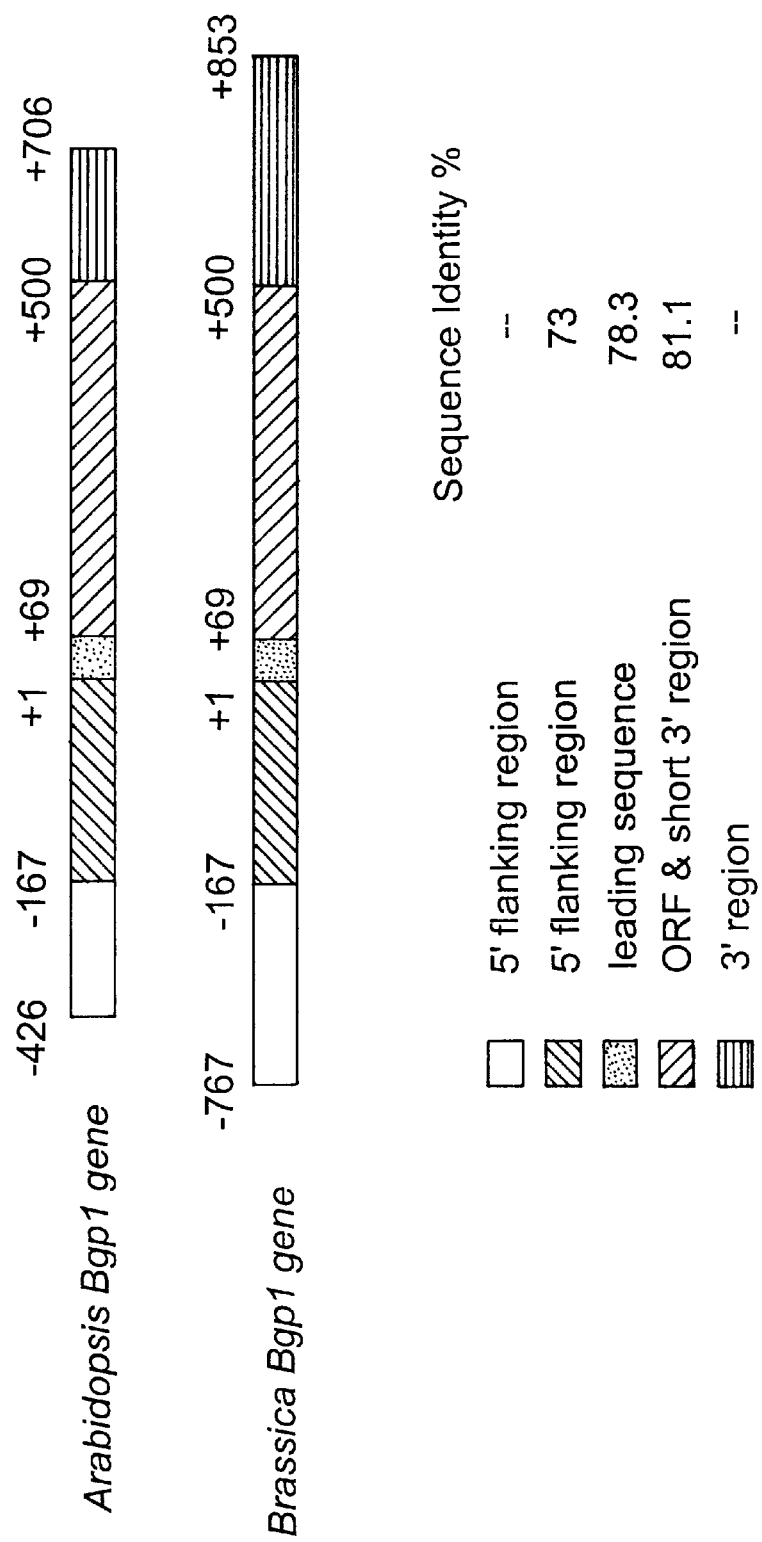

FIG. 11A is a diagram showing sequence identity between Arabidopsis Bgp1 gene and Brassica Bgp1 gene.

FIG. 11B is a representation of the nucleotide (SEQ ID NO. 8) and translated amino acid sequence (SEQ ID NO. 4) of the Arabidopsis Bgp1 gene. The sequence was determined by a genomic clone. The transcriptional initiation site determined by primter extension analysis was underlined (Xu, 1992). The longest open reading frame extends for 411 bp and translated into a 137 amino acids, approximately 14K protein with a highly hydrophobic region at N-terminus. A highly conserved (73% sequence identity) promoter region of 167 nucleotides which extends immediately upstream from the transcriptional initiation site was shared by the homologous genomic clone, Bgp1 from *Brassica campestris*.

The genomic clone was isolated by screening an *Arabidopsis thaliana* ecotype Landsberg erecta genomic library using a probe derived from a homologous Brassica cDNA clone, Bcp1. DNA sequencing was performed by dideoxy chain termination method using T7 DNA sequencing kit (Pharmacia LKB). Specific oligonucleotide primers were used to obtain the complete sequence. Sequence analysis was performed using the Melbot/Angis.

Figure 12A:
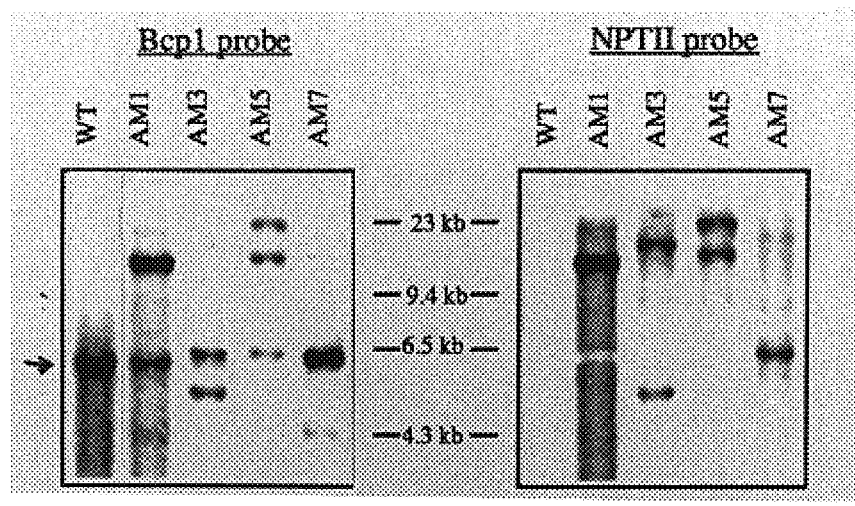
Figure 12B:
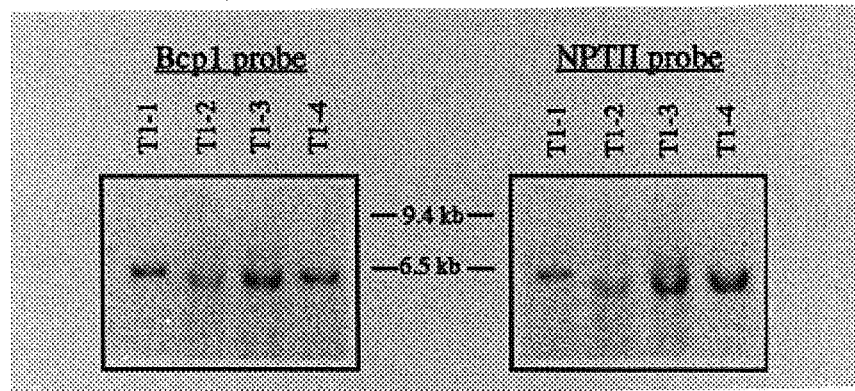
Figure 12C:
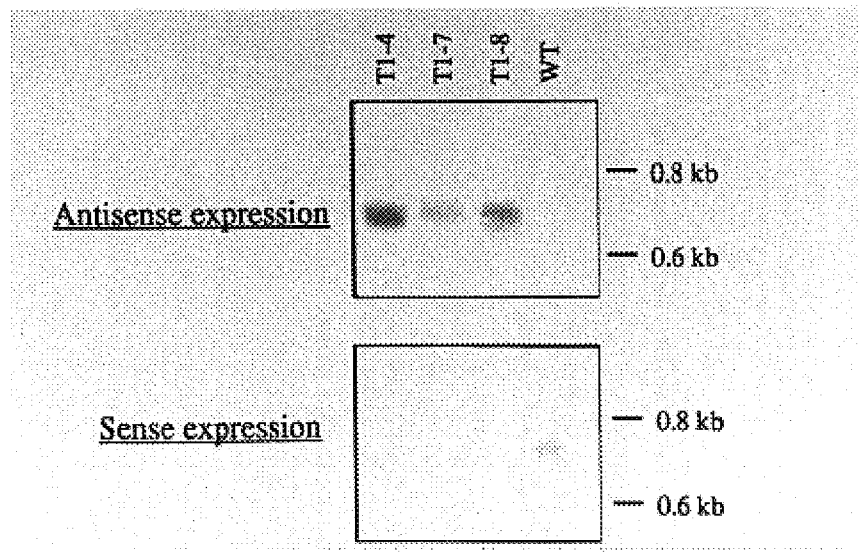
Figure 13A:
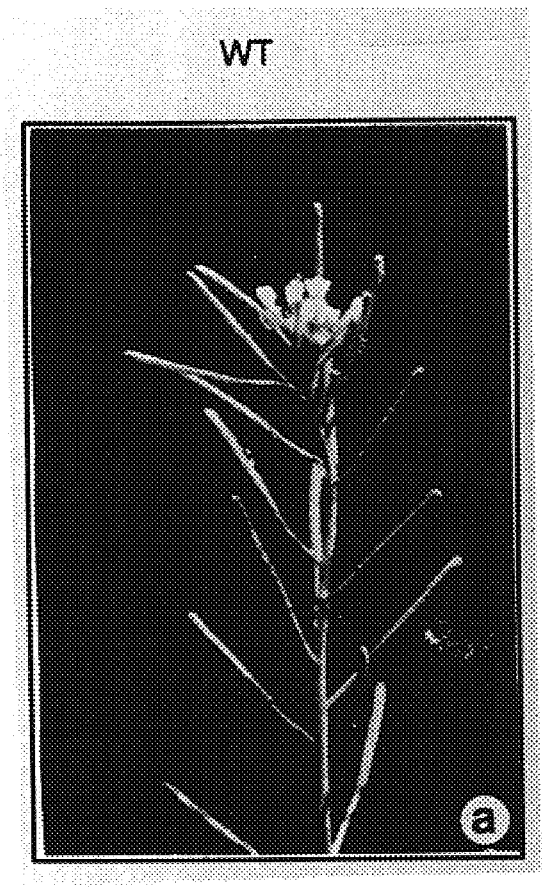
Figure 13B:
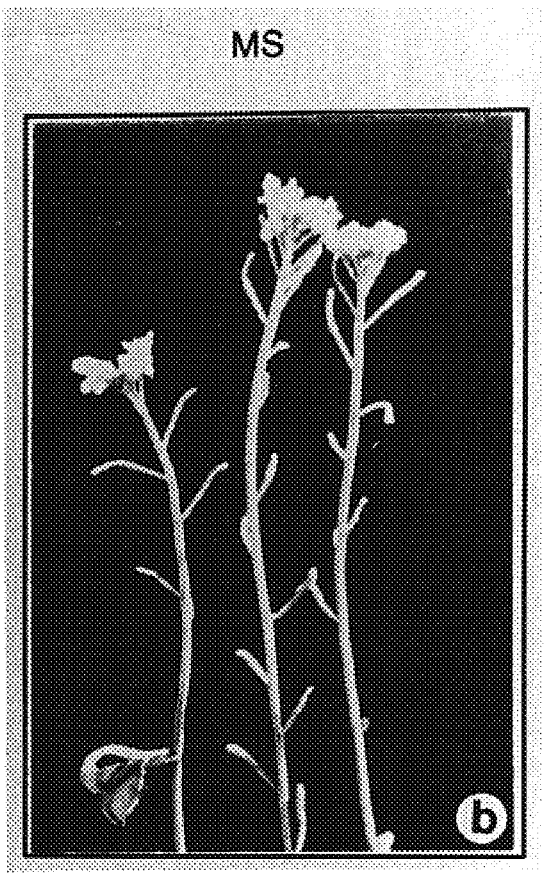
Figure 13C:
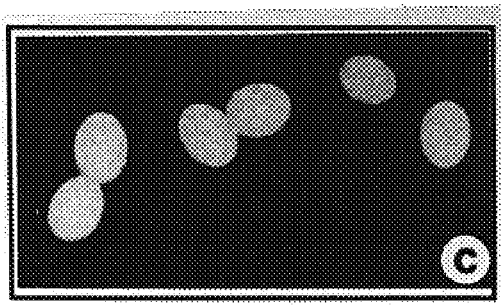
Figure 13D:
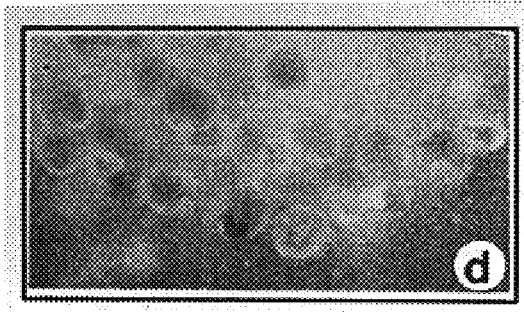

FIGS. 12A–12C are photographic representations of DNA and RNA gel blot analysis of antisense male sterile plants. (a) Detection of antisense insertions in the primary antisense transformants ($T_0$). Genomic DNAs from wild type (WT) and 4 individual antisense male sterile plants were used for parallel hybridisations with a Bgp1 gene-specific probe (left panel) and a kanamycin-resistant gene, NPTII, specific probe (right panel). A 6.3 kb fragment (arrowhead) showed hybridisation with the Bgp-1 specific probe but not with NPTII probe indicating that it contains the endogenous Bgp1 gene. The insertions of antisense constructs in transgenic plants were confirmed by the presence of DNA fragments which hybridised with both Bgp1 and NPTII probes. (b) DNA gel blot analysis of 4 individual $T_1$ plants showing the ineritance of the antisense gene. (c) RNA gel blot analysis of 3 individual $T_1$ plants. The expression of endogenous and antisense Bgp1 gene in $T_1$ plants. The expression of endogenous and antisense Bgp1 gene in $T_1$ plants was determined using specific probes. The endogenous sense Bgp1 transcripts were detected in the flowers of control wild type (WT) untransformed plants, but not in any of $T_1$ plants. The expression of the antisense Bgp1 gene was detected in the flowers of male sterile $T_1$ plants, but not in the untransformed wild type plants.

Primary transformants ($T_0$) carrying antisense Bcp1 gene were cross-pollinated with wild-type to produce seeds. The $T_1$ progenies were grown in the greenhouse. Genomic DNA was extracted from leaf tissues of appropriate plants and digested with Bam H1, which does not cut inside the Bcp1 gene. DNA fragments were separated on 0.7% w/v agarose gel (10 μg/lane) and transferred onto nylon membrane. The blots were hybridised with a $^{32}$P-labelled probe derived from the Bcp1 cDNA clone. Parallel blots were hybridised with a NPTII gene probe. mRNA were isolated directly from flower inflorescences using Daneal Beads. RNA gel blots were prepared as described (Maniatis et al., 1982). $^{32}$P-Labelled sense and antisense riboprobes were generated by in vitro transcription from the Bcp1 cDNA clone.

FIGS. 13A–13D are photographic representations of male sterile (MS) *Arabidopsis thaliana* (a) Flower inforescences from wild type (WT) plants. The plants produce elongated seed pods (Sp) resulted from self-pollination. Each seed pod yields 52–68 seeds. (b) Flower inflorescences from male sterile (MS) plants induced by transformation of the Bgp1 antisense gene. The male sterility is characterised by short and empty seed pods after self-pollination. (c) and (d) fluorochromatic reaction (FCR) test of pollen viability (Heslop-Harrison et al 1984). The viable pollen is characterised by the presence of bright fluorecence in pollen cytoplasm. Pollen grains from wild type plants showed 99% positive reaction (c), indicating high pollen viability, whereas pollen grains from male sterile plants gave no positive reaction (d), indicating that pollen is non-viable.

The Bcp1 antisense gene were constructed by inserting the 500 bp cDNA clone Bcp1 in the reversed orientation between an anther-specific promoter, Bgp1 and nonpaline synthase (nos) sequence. It was then cloned into a binary vector, Bin 19 (Bevan, 1984) and introduced into *Arabidopsis thaliana* (ecotype Landsberg erecta) using *Agrobacterium tumefaciens*-mediated transformation (Valvekens et al., 1988). The transformants were selected on medium containing kanamycin. Pollen grains from both wild type and transformed plants were stained with fluorescein diacetate and viewed with fluorescnece microscopy under UV excitation (Heslop-Harrison et al., 1984).

Figure 14A:
Figure 14B:
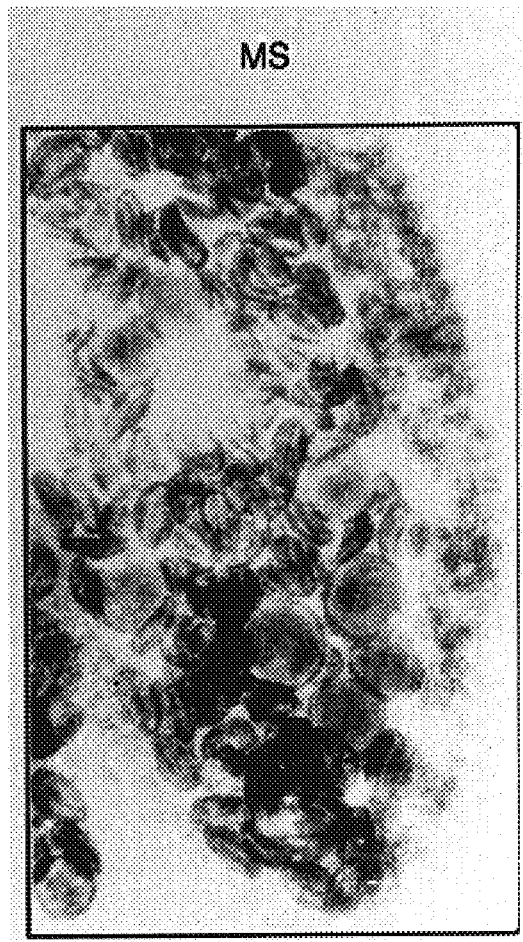

FIGS. 14A–14B are photographic representations showing differential staining of aborted and nonaborted pollen in nondehiscent anthers of male sterile plants using Alexander stain (Alexander, 1969). This stain differentially stains pollen walls (staining green) and pollen protoplasm (staining red). Anthers from wild type (WT) plants (FIG. 14A) contain regular, spherical pollen grains with intensive red staining in the protoplasm. In strong contrast with the fertile pollen from wild type plants, the majority of pollen grains (>90%) from male sterile (MS) antisense primary transformants (FIG. 14B) show only green staining of pollen walls indicating that the pollen grains are devoid of protoplasm and empty. The remaining grains had degenerated protoplasm as indicated by weak pink staining.

Figure 15A:
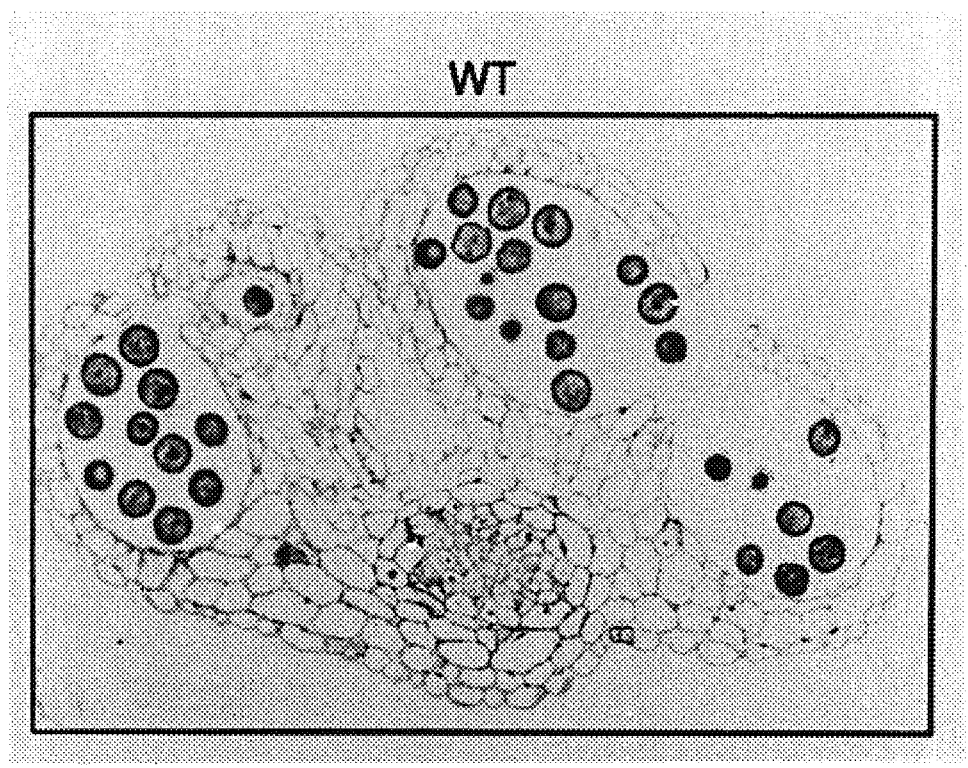
Figure 15B:
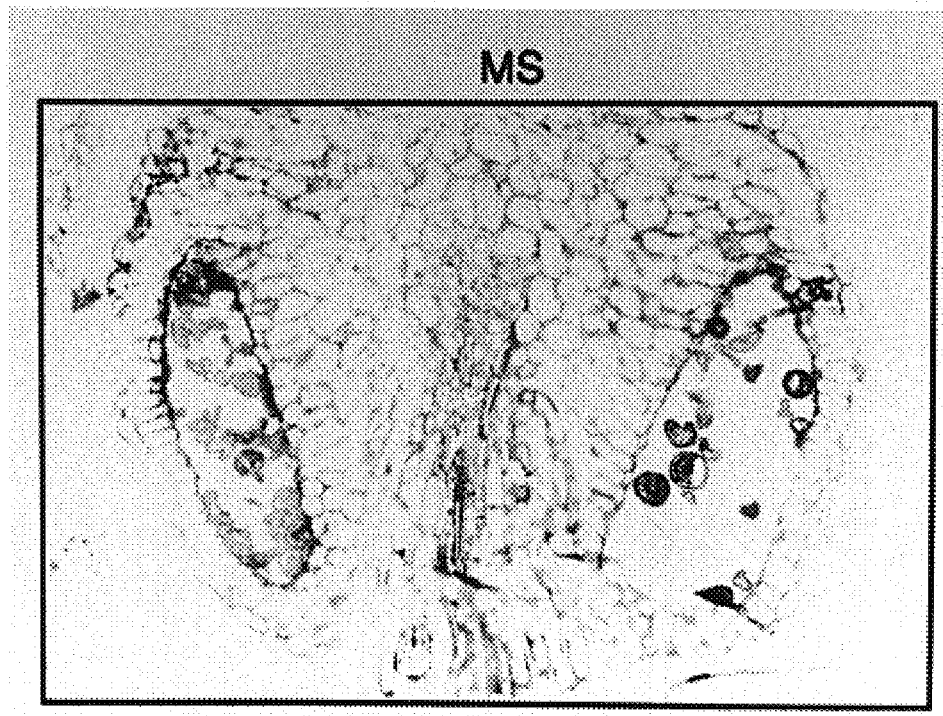
Figure 15C:
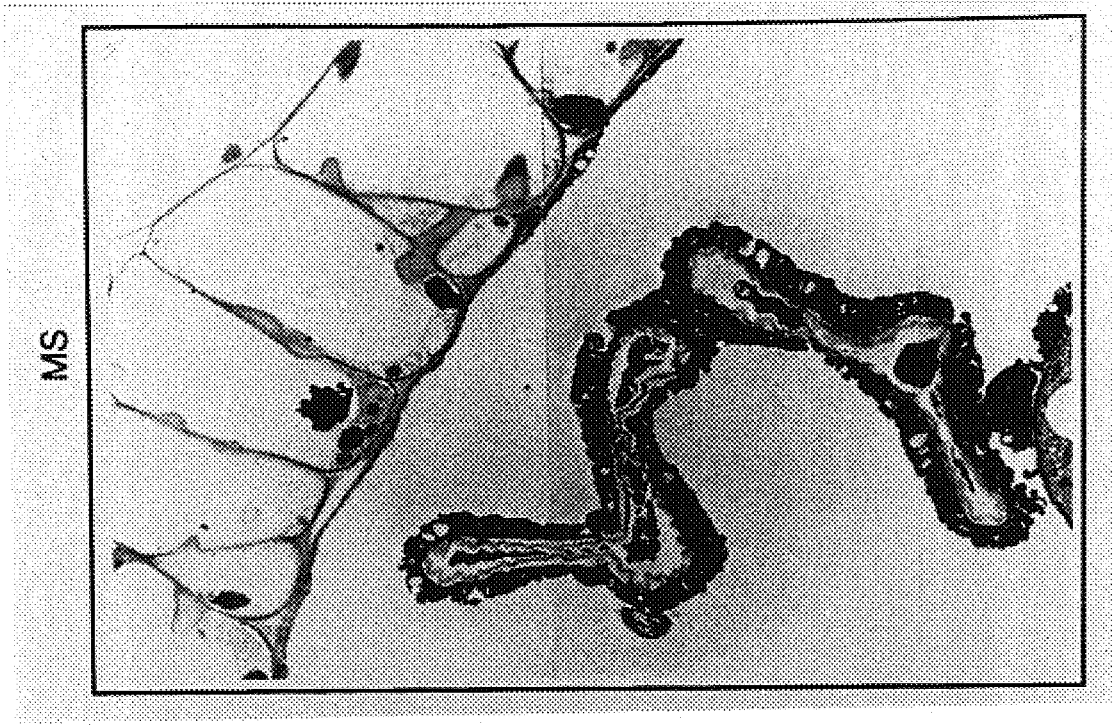
Figure 15D:
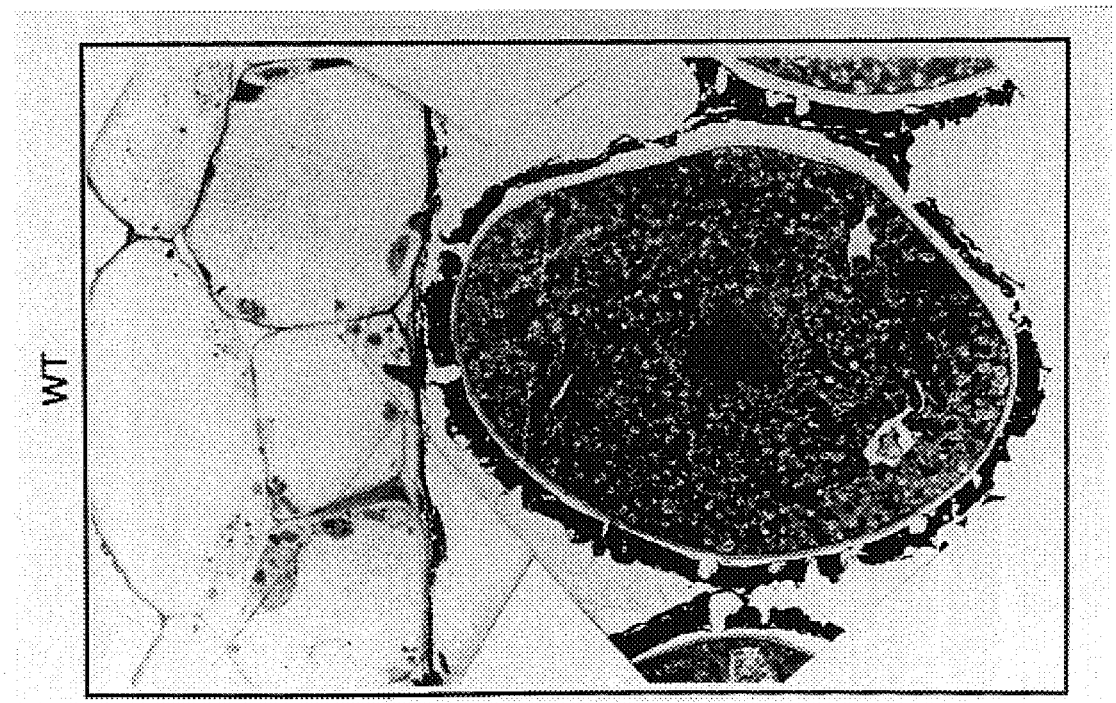
Figure 15E:
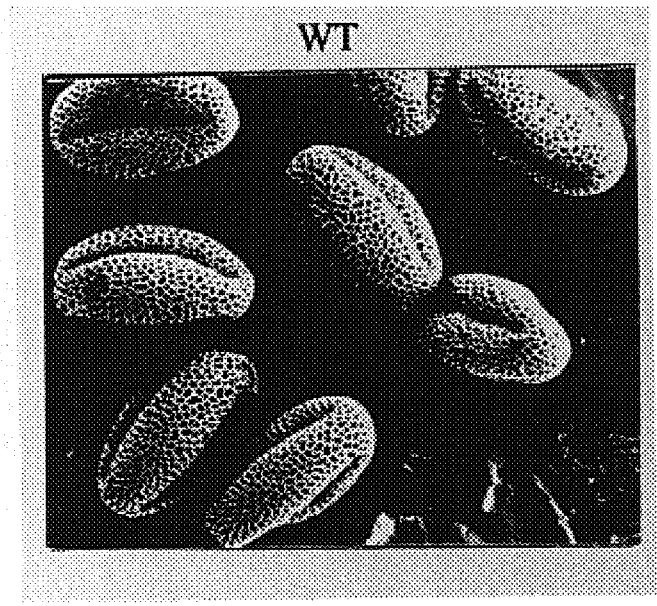
Figure 15F:
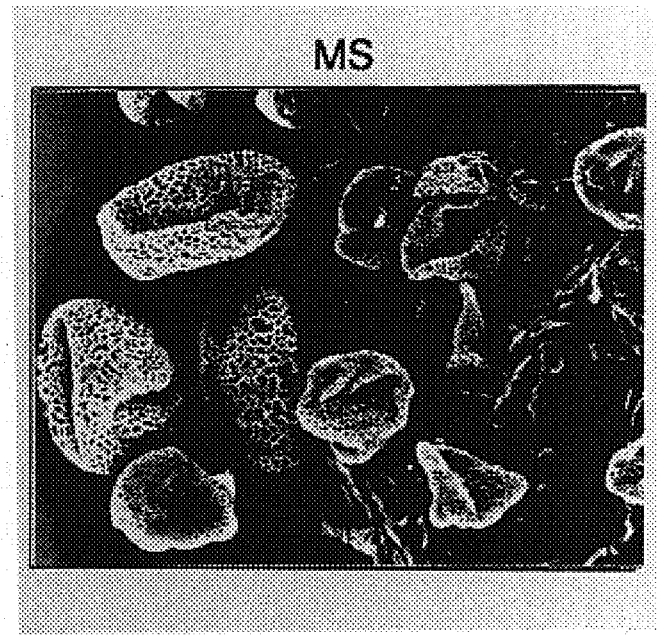

FIGS. 15–15F are photographic representations showing light and electron microscopic analyses of mature anthers from male sterile plants showing the abnormalities of pollen grains. FIGS. 15A and 15B are cross-sections of anthers from wild-type (WT) FIG. 15A, and male sterile antisense primary transformants (MS) FIG. 15B, shortly before dehiscencing. The majority of pollen grains in the anthers of male sterile plants has no internal protoplasm confirming the observation obtained by Alexander stain in FIG. 14. FIGS. 15C and 15D are transmission electron microscopic (TEM) studies of pollen from wild type (FIG. 15D) and antisense male sterile (FIG. 15C) plants. The male sterile pollen was completely empty and only the crushed exines are present. FIGS. 15E and 15F are scanning electron microscopic (SEM) studies of fertile pollen from wild type plants (FIG. 15E) and sterile pollen from antisense plants (FIG. 15F).

Mature flowers were fixed in 2% glutaradehyde and postfixed in 1% osmium, tetraxide. After dehydration through an enthanol series, the flowers were embedded in Spur resin and sectioned. For light microscopy, semi-thin sections (1 μm) were stained with toluidine blue and mounted. For TEM, ultra-thin sections were stained and viewed following standard procedure. For SEM observation, dehiscencing anthers were mounted on stab and air dried in a desiccator. The samples were observed after gold sputtering.

The following is a summary of the SEQ ID NOs referred to in the subject specification. The SEQ ID NOs are defined in full after the bibliography.

SUMMARY OF SEQ ID NOs

| | |
|---|---|
| SEQ ID NO. 1 | Open reading frame of *B. campestris* Bgp1 |
| SEQ ID NO. 2 | Deduced amino acid sequence of SEQ ID NO. 1 |
| SEQ ID NO. 3 | Open reading frame of *A. thaliana* Bgp1 |
| SEQ ID NO. 4 | Deduced amino acid sequence of SEQ ID NO. 3 |
| SEQ ID NO. 5 | Promoter region of *B. campestris* Bgp1 |
| SEQ ID NO. 6 | Promoter region of *A. thaliana* Bgp1 |
| SEQ ID NO. 7 | *B. campestris* Bgp1 |

-continued

SUMMARY OF SEQ ID NOs

| | |
|---|---|
| SEQ ID NO. 8 | *A. thaliana* Bgp1 |
| SEQ ID NO. 9 | *B. campestris* Bgp1 modified promoter −767 to −116 |
| SEQ ID NO. 10 | Bgp1 specific oligonucleotide |
| SEQ ID NO. 11 | Bgp1 oligonucleotide |
| SEQ ID NO. 12 | Bgp1 TATA box sequence |
| SEQ ID NO. 13 | Consensus Bgp1 sequence |

DETAILED DESCRIPTION OF THE INVENTION

EXAMPLE 1

CLONING OF BRASSICA Bgp1

Construction of genomic library, screening and isolation of the genomic clone Bgp1. A genomic library was prepared from leaf material of *Brassica campestris* cv. T15. Genomic DNA was isolated according to standard procedures (Murray et al., 1980) and partially digested with Sau 3A. Sau 3A fragments were size fractionated on a glycerol gradient (10–40%) by centrifugation at 40,000 rpm overnight. Aliquots of 500 μl fractions were taken and diluted 1:2 in TE buffer (10 mM TRIS-HCI, pH8.0; 1 mM EDTA). DNA from the chosen fractions was then recovered by precipitation with ethanol and centrifugation at 13,000 g for 30 minutes. The resultant 9–23 kb fragments were ligated into EMBL3 Bam H1 arms (Stratagene). The ligation mix was then packaged into phage using Packagene (Promega Biotec.) to yield the genomic library. The library was plated on LB media at a density of approximately 10 000 plaques per 90 mm plate using *Escherichia coli* NW2 (Woodcock et al., 1988) as the host strain. Duplicate plaque lifts were performed using Hybond-C extra following the manufacturer's protocol. The filters were hybridized with $^{32}$P-labelled Bgp1 in 2×SSPE, 0.5% w/v Blotto, 1% w/v PEG 20 000, 7% w/v SDS and 250 mg/ml (final volume) denatured Herring sperm DNA at 65° C. Filters were washed at 65° C. for 30 minutes in 2×SSC, 0.1% w/v SDS and for 15 minutes in 0.2×SSC, 0.1% w/v SDS. Filters were exposed to Kodak X-Omat film overnight at −70° C. The genomic clone obtained is designated "Bgp1".

DNA Sequencing.

A series of overlapping deletion clones (Bgp1.1–Bgp1.7) were generated from the Bgp1 4.2 kb HindIII genomic fragment by digestion with Exonuclease III and religation. The protocols supplied with the Nested Deletions kit (Pharmacia LKB) were followed. Southern blot analysis demonstrated that Bgp1.1–Bgp1.5 but not Bgp1.6 and Bgp1.7 show homology to Bgp1. Sequencing then commenced using Bgp1.1 though Bgp1.5 as templates. Sequencing reaction was performed on double-stranded template according to the T7 polymerase sequencing kit manual (Pharmacia LKB). Both strands were sequenced using T7, SP6 or synthetic primers made to internal sequences.

RNA and DNA Gel Blot Analyses.

RNA gel blot hybridizations were performed using total RNA (20 μg per lane) separated by electrophoresis on formaldehyde-agarose gels and blotted onto Hybond-N (Amersham) nylon filters (Maniatis et al., 1982). Filters were prehybridized, hybridized with $^{32}$P-labelled oligonucleotide and washed according to the manufacturers specifications (Amersham). DNA gel blots were performed using 10 μg of *B. campestris* DNA per digest separated on 0.8% w/v agarose gels and blotted onto Hybond-N filters following standard protocols (Maniatis et al., 1982). Prehybridization, hybridization with $^{32}$P-labelled DNA and washing was again done according to the manufacturer's specifications (Amersham).

Primer Extension Analysis.

The transcriptional start point of Bgp1 was determined by primer extension analysis performed according to standing procedures (Maniatis et al., 1982). A 15-mer synthetic oligonucleotide of sequence 5'-CGTTTTGGCGACCCA-3' (SEQ ID NO. 11) complementary to nucleotides 22–36 of Bgp1 was end-labelled with [g$^{32}$P] ATP (Amersham) and T4 polynucleotide kinase (Promega Biotech). After annealing and extension of the primer, the products were analysed on a polyacrylamide sequencing gel.

Construction of Plasmids.

The 0.8 kb P st I-Hae III DNA fragment (from position −767 to +100 including the 0.7 kb 5' flanking region and 100 nucleotides of the 5' untranslated leader sequence of the Bgp1 gene), was excised from Bgp1.3, a deletion clone of Bgp1, and ligated to Bluescript (+) KS (Stratagene). This fragment was then excised as a HindIII-Bam HI fragment and inserted into the polylinker of the vector, pBI 101 (Stratagene). This vector is a derivative of the binary vector pBIN 19 (Bevan, 1984) which contains a promoter-less gus gene cassette (Jefferson et al., 1986) fused to the nopaline synthase polyadenylation region. The resulting Bgp1-GUS chimeric construct, designated as pBgp1.2, was mobilized into *Agrobacterium tumefaciens* strain LBA 4404, by conjugating with a helper plasmid pRK 2013 (Koncz and Schell, 1986).

Plant Transformation.

(i) Tobacco: leaf discs of *Nicotiana Tabacum* var. Wisconsin 39 were transformed with *Agrobacterium tumefaciens* essentially as described in Horsch et at. (1985). Shoots arising from leaf discs were rooted on MS medium (Gibco Laboratory) containing 1.0 μg/ml IAA, 1.0 μg/ml BAP, 100 μg/ml Kanamycin, transferred to soil and grown to flowering in the greenhouse. *Arabidopsis thaliana* var Landsberg roots were transformed according to Valvekens et al. (1985). Transgenic plants were selected on medium containing 50 μg ml$^{-1}$ kanamycin.

GUS Assay.

Histochemical GUS assays were performed essentially as described by Jefferson et al. (1987). For histochemical assay, plant materials were placed in the wells of a microtiter plate containing 1 mM X-Glu (5-bromo-4-chloro-3-indolyl-β-D-glucuronic acid, Sigma) in 0.1 M NaPO$_4$pH 7.0, 0.1% v/v Triton-X 100 and incubated at 37° C. for 8 to 12 h. In Arabidopsis, the positively stained flowers were processed for cryo-sectioning. The samples were embedded, rapidly frozen in Tissue-Tek OCT compound (Miles Inc., Elkhart, Ind.) and sectioned at −20° C. using a 2800 Frigocut cryostat (Reicher-Jung, Germany). The developmental stages of anthers were determined by staining the sections with DAPI (Coleman and Goff, 1984).

Genomic Clone Bgp1 is Highly Homologous to the cDNA Clone Bcp1.

A genomic clone, designated Bgp1 was isolated from *Brassica campestris* using cDNA clone Bcp1 as a probe. A partial restriction endonuclease site analysis of the 11 kb genomic fragment in Bgp1 resulted in the map presented in FIG. 1. Southern blot analysis using Bcp1 as a probe revealed that a 4.2 kb Hind III fragment from the 11 kb genomic clone contained the coding region of the gene. This fragment was then subcloned and partially sequenced.

A total of 1620 bp of DNA was determined, this included the entire sequence of the coding region along with 767 bp of 5' flanking sequence. Comparison of the cDNA sequence of Bcp1 (Theerakulpisut et al., 1991) with the coding region of genomic clone Bgp1 revealed an overall homology of 88%. No introns are present. The sequence of the Bgp1 coding region, 767 bp of 5' flanking region and 392 bp of 3' flanking region is presented in FIG. 1.

EXAMPLE 2

TISSUE-SPECIFIC EXPRESSION OF Bgp1 ENDOGENOUS GENE

Figure 2:
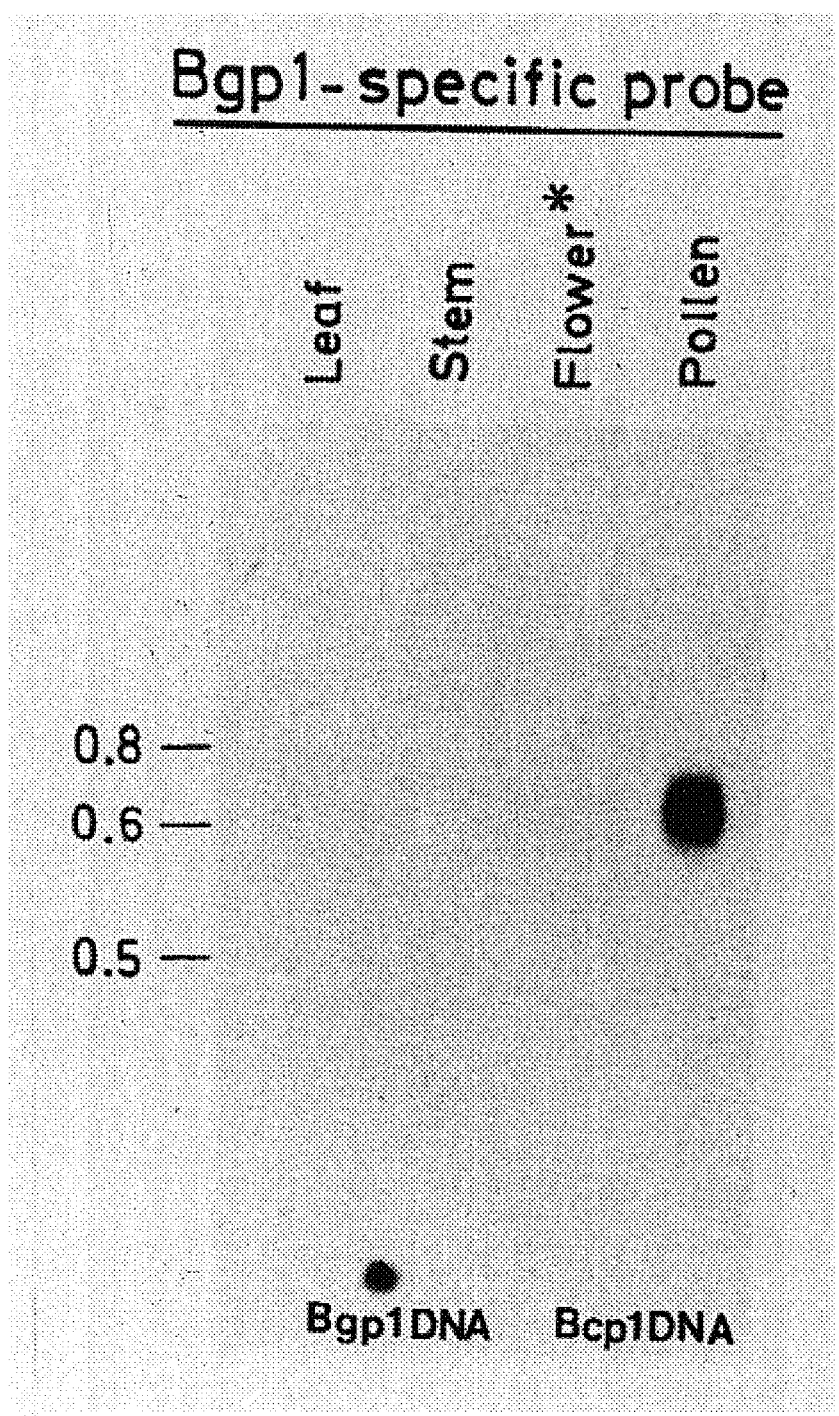
FIG. 2 is a photographic representation showing Bgp1 expression pattern in different organs of B. campestris. RNA transcripts are detectable only in pollen. Total RNA isolated from leaves, stems, flower minus anther and pollen was fractionated on a denatured agarose gel (20 $\mu$g per lane), transferred onto a nylon membrane and probed with a Bgp1 specific oligonucleotide (based on the sequence between nucleotides 181–201; 5'-GGCTGCTACCGTAACCGATGT-3' [SEQ ID NO. 10]) labelled with $^{32}$P. Bgp1 DNA and Bcp1 DNA,were also probed to verify the specificity of the oligonucleotide, hybridisation was only observed to DNA from the clone Bgp1 as indicated.

In order to determine the expression pattern of Bgp1 gene, a Bgp1-specific oligonucleotide was synthesized based on the sequence, between nucleotides 181–201 (5'-GGCTGCTACCGTAACCGATGT-3' [SEQ ID NO. 10]) (FIG. 1), a region which shows a high level of variability between the two genes, Bgp1 and Bcp1. This 21 mer oligonucleotide was used to probe a Northern blot containing total RNA isolated from *B. campestris* pollen, leaf, stem, and flower (minus anther). As a negative control Bcp1 DNA was included on the blot to ensure the specificity of the oligonucleotide. FIG. 2 shows that the Bgp1-specific oligonucleotide hybridizes to RNA present in pollen but not to RNA present from any other tissue tested. The size of the transcript=700 nucleotides is approximately the same size as the RNA transcript to which clone Bcp1 hybridizes (Theerakulpisut et al., 1991).

EXAMPLE 3

Bgp1 BELONGS TO A SMALL GENE FAMILY

Figure 3:
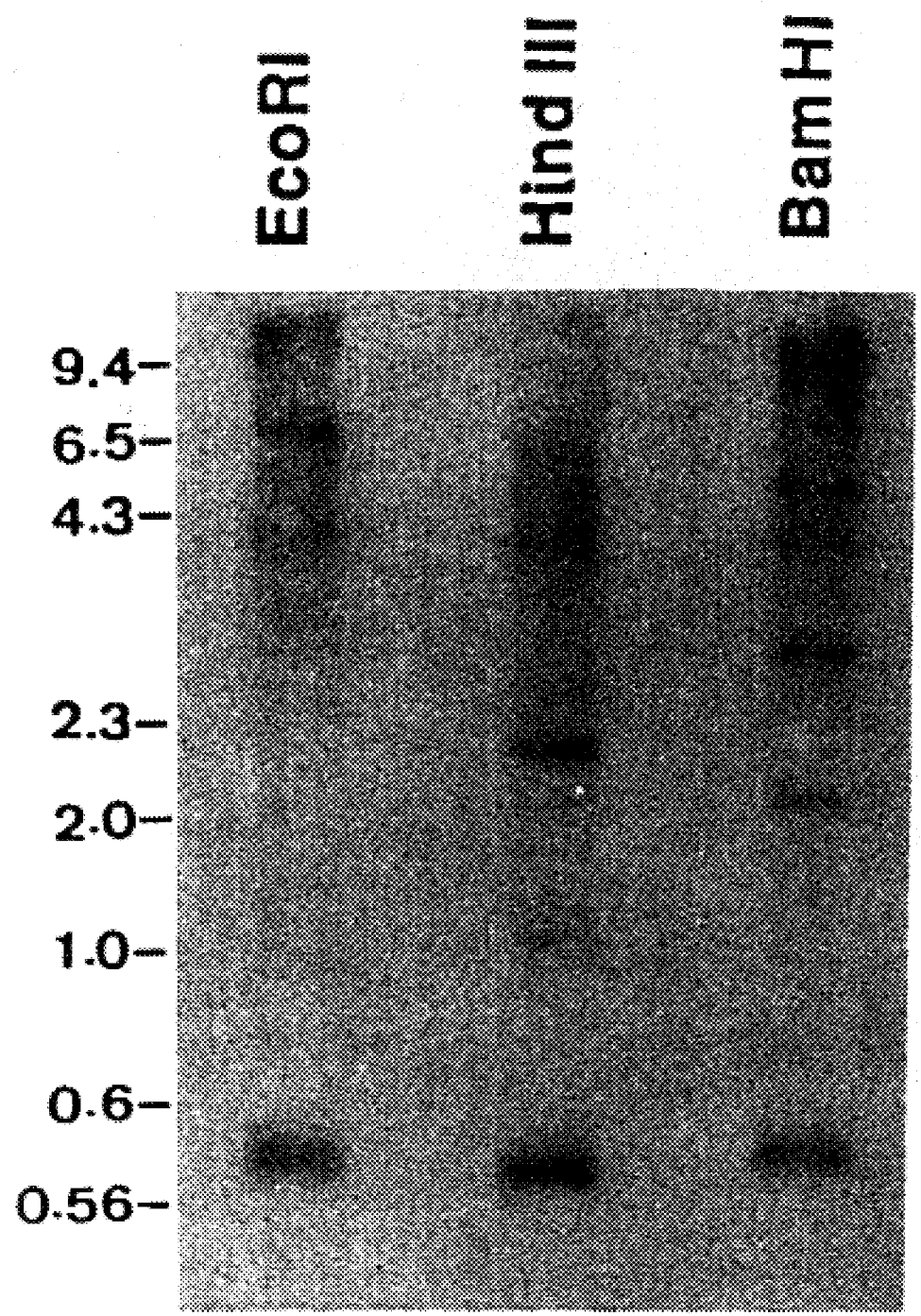
FIG. 3 is a photographic representation of DNA gel blot analysis of genomic DNA isolated from B. campestris. Genomic DNA was digested with the restriction endonucleases EcaRI, HindIII and BamHI as indicated and probed with $^{32}$P-labelled Bcp1 DNA The position of HindIII digested 1 DNA is indicated.

To determine whether the clone Bcp1 represents a transcript from a member of a gene family, the cDNA insert was used to probe a DNA gel blot of total *B. campestris* DNA. FIG. 3 shows that Bcp1 cDNA insert hybridizes to several genomic bands including the 4.2 kb Hind III fragment representing the Bgp1 gene. It is difficult to estimate the gene family copy number from this blot but there are at least two members in the gene family.

EXAMPLE 4

DETERMINING THE TRANSCRIPTIONAL START OF Bgp1

Figure 4:
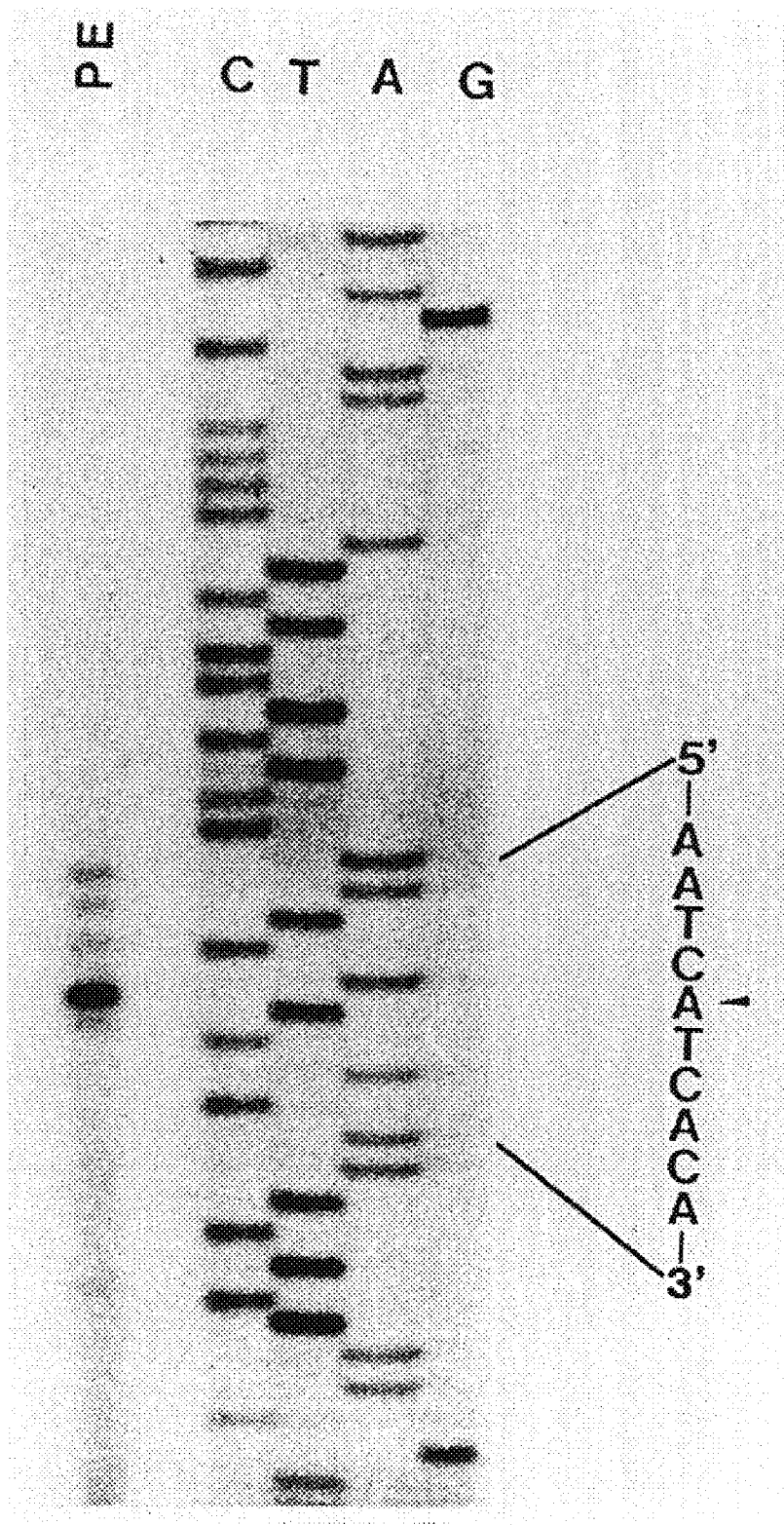
FIG. 4 is a photographic representation identifying the transcriptional start of the Bgp1 gene. Primer extension and plasmid sequencing (G, A, T, C) were performed using a synthetic oligonucleotide with sequence 5'-CGTTTTGGCGACCCA-3' (SEQ ID NO. 11) which is complementary to nucleotides 22–36. The nucleotide sequence at the 5' end is reported. The arrow indicates the position of the major extension product.

The transcriptional start point of Bgp1 was determined by primer extension analysis. An oligonucleotide was synthesized based on the sequence between nucleotides 22–36 (FIG. 1). FIG. 4 shows that when this primer was used in extension analysis and the labelled products run next to the sequence of clone Bgp1, a fragment of length 61 nucleotides can be detected. This indicates that the A nucleotide at position 1 (FIG. 1) is the first nucleotide transcribed from the Bgp1 gene. Fainter bands are likely to be due to homologous transcripts from other members of the Bcp1 gene family.

EXAMPLE 5

SEQUENCE ANALYSIS

The promoter region of the Bgp1 gene contains a TATA box sequence (CAACTATATATAG [SEQ ID NO. 12]) which is located 26 nucleotides upstream of the start of transcription (see FIG. 1). In agreement with the "scanning mechanism" theory (Kozak, 1986), the translational start of the Bgp1 gene is the first ATG codon present in the sequence, which is found 69 nucleotides downstream from the start of transcription (FIG. 1). The putative start codon gives the longest possible open reading frame (357 nucleotides) and its flanking regions match perfectly with the consensus proposed for plant genes of AACAATGGC [SEQ ID NO. 13] (Lutcke et al., 1987). The resulting untranslated leader sequence is characteristically A/T rich (63%).

The predicted protein sequence of clone Bgp1 is shown under the nucleotide sequence in FIG. 1. The Bgp1 protein sequence is very similar to the predicted protein sequence from Bcp1 (Theerakulpisut et al., 1991) showing 87.5% identity. A computer search comparing the nucleotide and amino acid sequence of clone Bgp1 with the sequences contained in GenBank, EMBL and NBRF databases revealed no significant homologies.

The 5' upstream region of clone Bgp1 was examined for homology to the promoter regions of both anther and pollen specific genomic clones. A comparison of the entire 767 bp Bgp1 5' region was made with a range of 5' sequences from pollen/anther specific genes (Hamilton et al., 1989; Twell et al., 1989, 1991; Koltunow et al., 1990; Albani et al., 1991a, 1991b). No significant regions of homology were observed.

EXAMPLE 6

TRANSFORMATION OF THE FULL LENGTH PROMOTER CONSTRUCT INTO ARABIDOPSIS—HIGH LEVELS OF GUS ACTIVITY PRESENT IN POLLEN AND TAPETUM

The histochemical distribution of the GUS activity driven by the 767 bp Bgp1 5' region carried by the construct pCB1.2 is illustrated in FIG. 5. FIG. 5A shows that high levels of GUS activity were present in anthers, but not in petals, sepals, filaments and pistils. No GUS activity was detected in anthers of control untransformed plants.

Figure 5A:
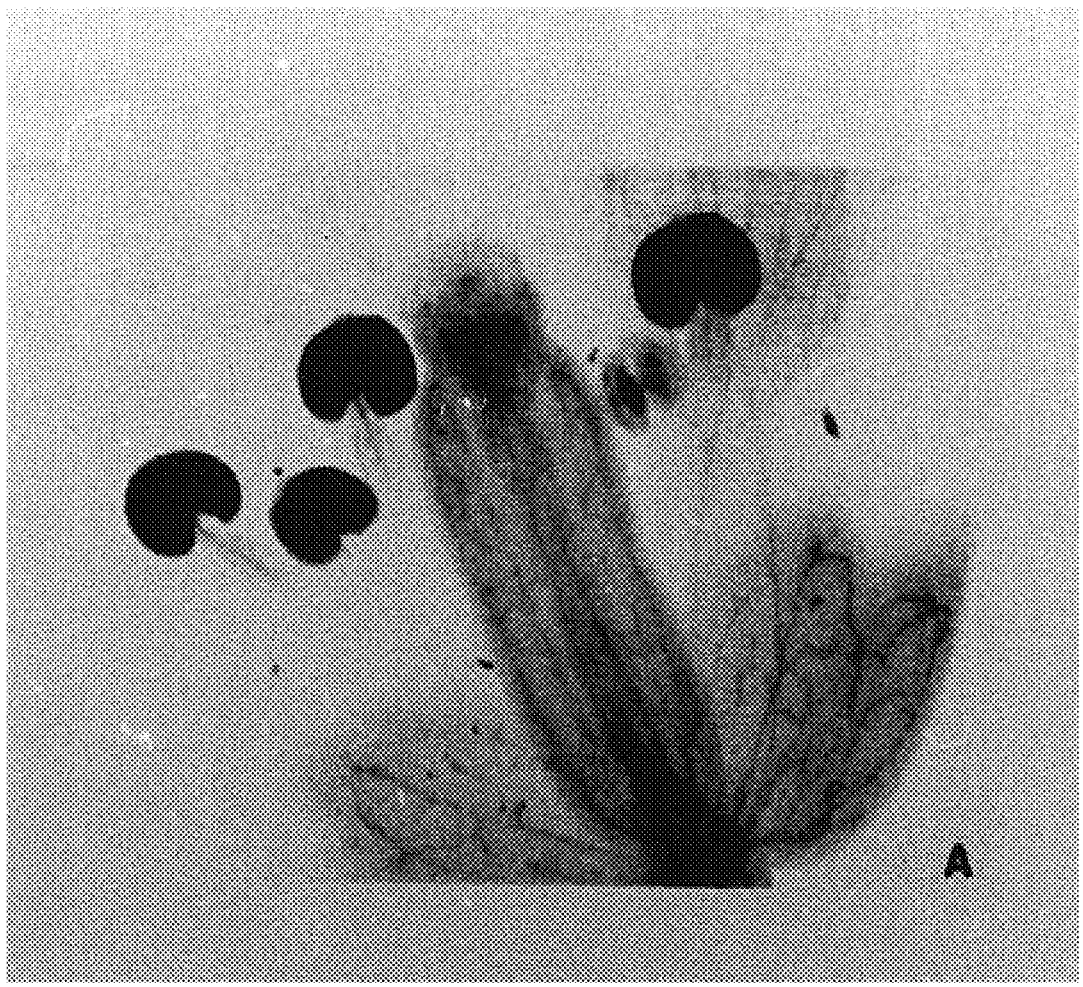
FIGS. 5A–5J show a histochemical detection of GUS activity in-transgenic Arabidopsis (FIGS. 5A–5H) and tobacco (FIGS. 5I–5J). GUS activity is indicated by blue staining (Jefferson et al., 1986). A. mature flower showing the distribution of GUS activity. B, C, longitudinal section of a flower bud containing anthers at early bicellular stages, showing high level of GUS activity in tapetum (arrow heads). D. cross section of a near mature another showing GUS activity in degenerating tapetum (arrow heads) and pollen. E. cross section of an anther from control untransformed plants. F. cross section of a mature anther showing GUS activity in pollen, but not in other anther tissues. G. GUS staining in mature pollen. H. pollen of control untransformed plants. I. mature pollen of transgenic tobacco. J. mature pollen of control untransformed tobacco.
Figure 5B:
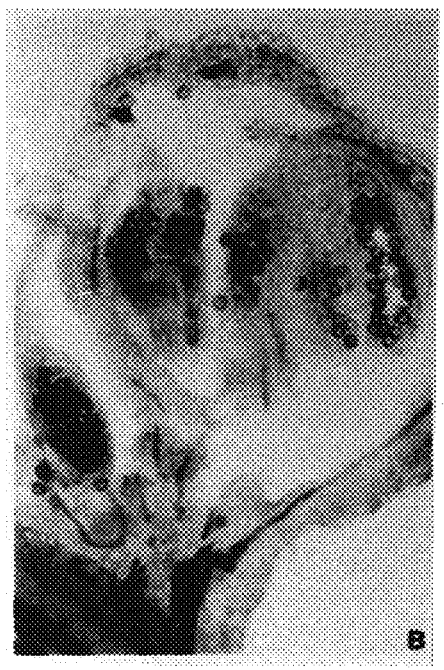
Figure 5C:
Figure 5D:
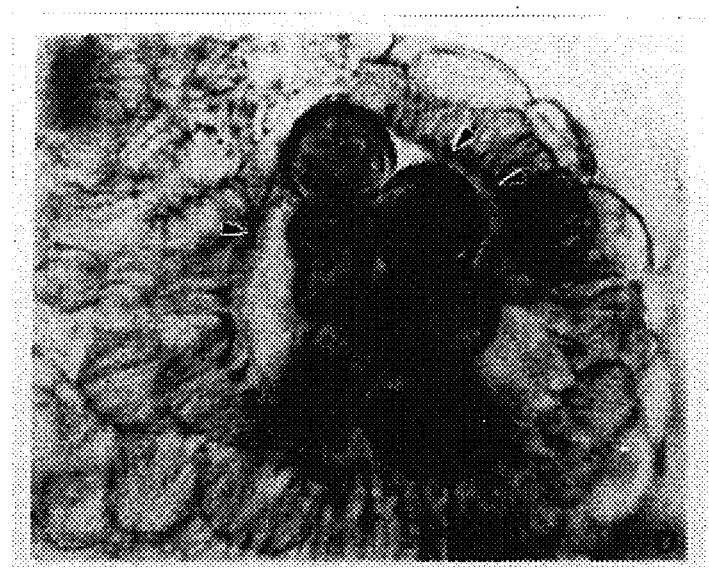
Figure 5E:
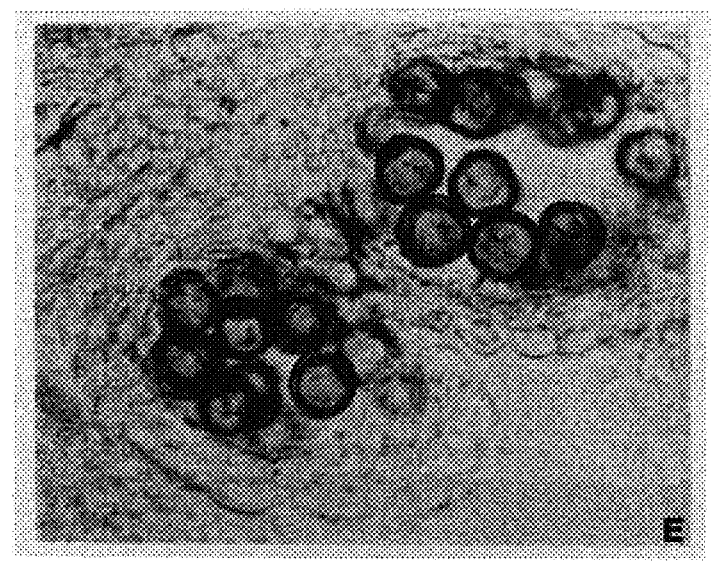
Figure 5F:
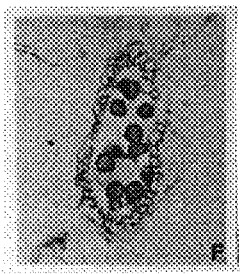
Figure 5G:
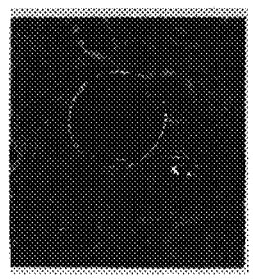
Figure 5H:
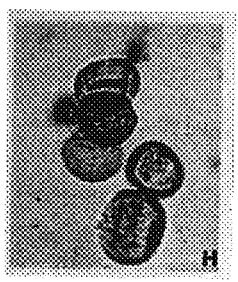

The developmental pattern of Bgp1-promoter activity was also analysed in transgenic plants carrying the construct pCB1.2. In cryosections of developing Arabidopsis anthers containing an intact tapetum, FIGS. 5B and 5C show that high levels of GUS activity were present in the tapetum, whereas only low levels were detactable histochemically in the pollen at early bicellular stage. In near mature anthers, in which the tapetum had begun to degenerate, FIG. 5D shows that high levels of GUS activity were present both in the degenerating tapetum and pollen grains. FIGS. 5F and 5G show that very high levels of GUS activity were present in mature pollen, but not in other tissues of the anther. FIGS. 5E and 5H show that tissues of control untransformed anthers and pollen produced no histochemically detectable levels of GUS activity.

EXAMPLE 7

TRANSGENIC TOBACCO PLANTS SHOW GUS ACTIVITY IN POLLEN ONLY

Figure 5I:
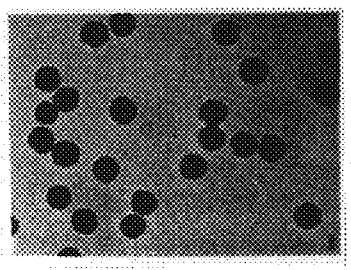
Figure 5J:
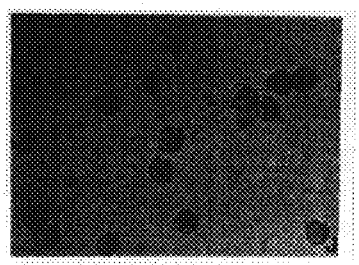

In transgenic tobacco plants carrying pCB.2, GUS activity was detected in pollen (FIG. 5I). In addition GUS activity was tested in anther sections taken from flower buds at several developmental stages. In tobacco, flower bud length correlates well with gametophytic development (Koltunow et al., 1990). Sections were taken from flower buds of sizes 3 mm (tapetum formation commences), 4 mm (tapetum and pollen sacs distinct), 5 mm (meiosis begins), 6 mm (tapetum large and multinucleate), 7 mm, 8 mm (meiosis complete) through to 14 mm (tapetum shrunken, pollen grains begin to form). No GUS activity was detected in the tapetum at any of these developmental stages.

EXAMPLE 8

ANALYSIS OF BGP1 5' PROMOTER DELETIONS

Figure 6:
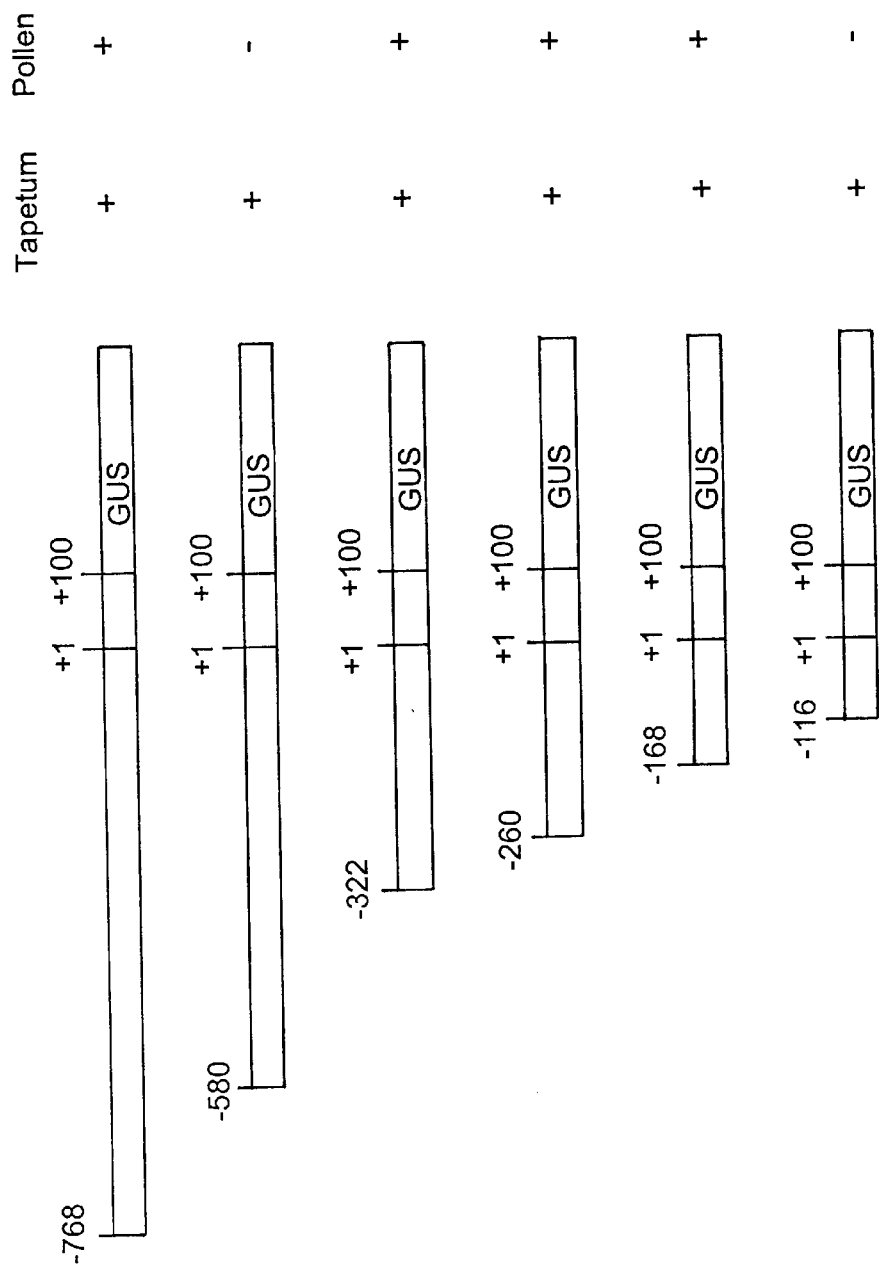
FIG. 6 shows Bgp1 5' deletion fragments. Each of the fragments shown were fused to the GUS gene in the vector pBI101 and introduced into *Arabidopsis thaliana*. The full length promoter fragment pBC1.2 was also introduced into *Nicotiana tabacum*. Next to each promoter fragment is the GUS expression pattern observed for each corresponding pBI101 construct in *A. thaliana*.
Figure 7:
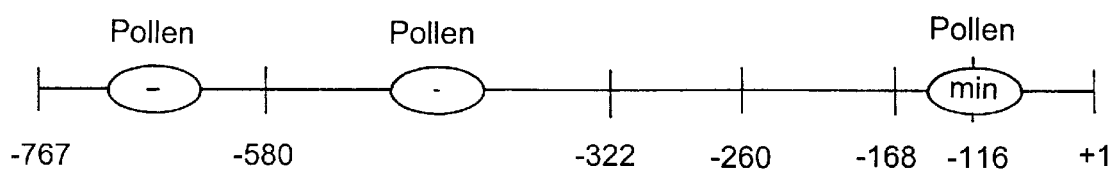
FIG. 7 is a working model showing the likely location of cis-acting DNA elements controlling the expression of the Bgp1 gene in pollen and tapetum. A+ indicates this region has a positive effect on expression and − signified a negative effect. The term min signifies the minimal promoter region necessary for pollen expression.

To identify cis-acting elements controlling the temporal and spatial expression pattern of Bgp1 a series of 5' deletion clones were created. These constructs, shown in FIG. 6, were transferred to *Arabidopsis thaliana* by *Agrobacterium tumefaciens* mediated transformation. GUS activity was analysed on primary transformants. At least 10 individual transformants were analysed for each construct. The GUS expression pattern for each of the constructs is presented alongside each of FIG. 6.

Deletion of the full length promoter down to −580 (pCB1.3) abolished any detectable GUS expression in the pollen of 87% of the plants tested. Expression in the tapetum of plants carrying pCB1.3 was unaffected. However, if further deletion removed the region between −322 and −580 (pCB1.4), GUS expression in the pollen was restored in all the plants tested. Progressive 5' deletions down to −260 (pCB1.5) and −168 (pCB1.6) gave the same result, GUS expression was observed in both the tapetum and the pollen. The smallest construct tested however, which contained only the 5' region up to position −116, directed GUS expression in the tapetum only.

EXAMPLE 9

INDUCING MALE STERILITY IN ARABIDOPSIS BY ANTISENSE

Construction of Antisense Gene

Figure 8:
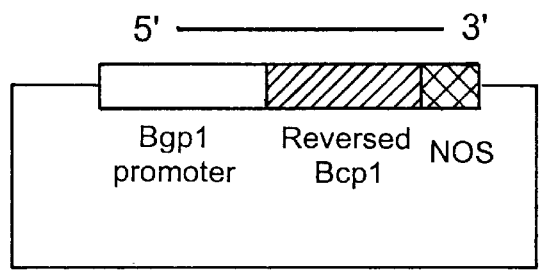
FIG. 8 is a diagramatic representation showing Bgp1 antisense construct.

A Bcp1 antisense gene was constructed by inserting the cDNA clone Bcp1 in the reverse orientation between an anther-specific promoter,. Bgp1 and nopaline synthase (nos) sequence. It was then cloned into the plant transformation vector, Bin 19 (FIG. 8). The resulting construct was mobilised to *Agrobacterium tumefacien* strain LBA 4404 and introduced into *Arabidopsis thaliana* var Landsberg using standard procedures (Valvekens et al., 1988). The transgenic plants carrying the antisense construct were selected by Kanamycin resistance.

Figure 9:
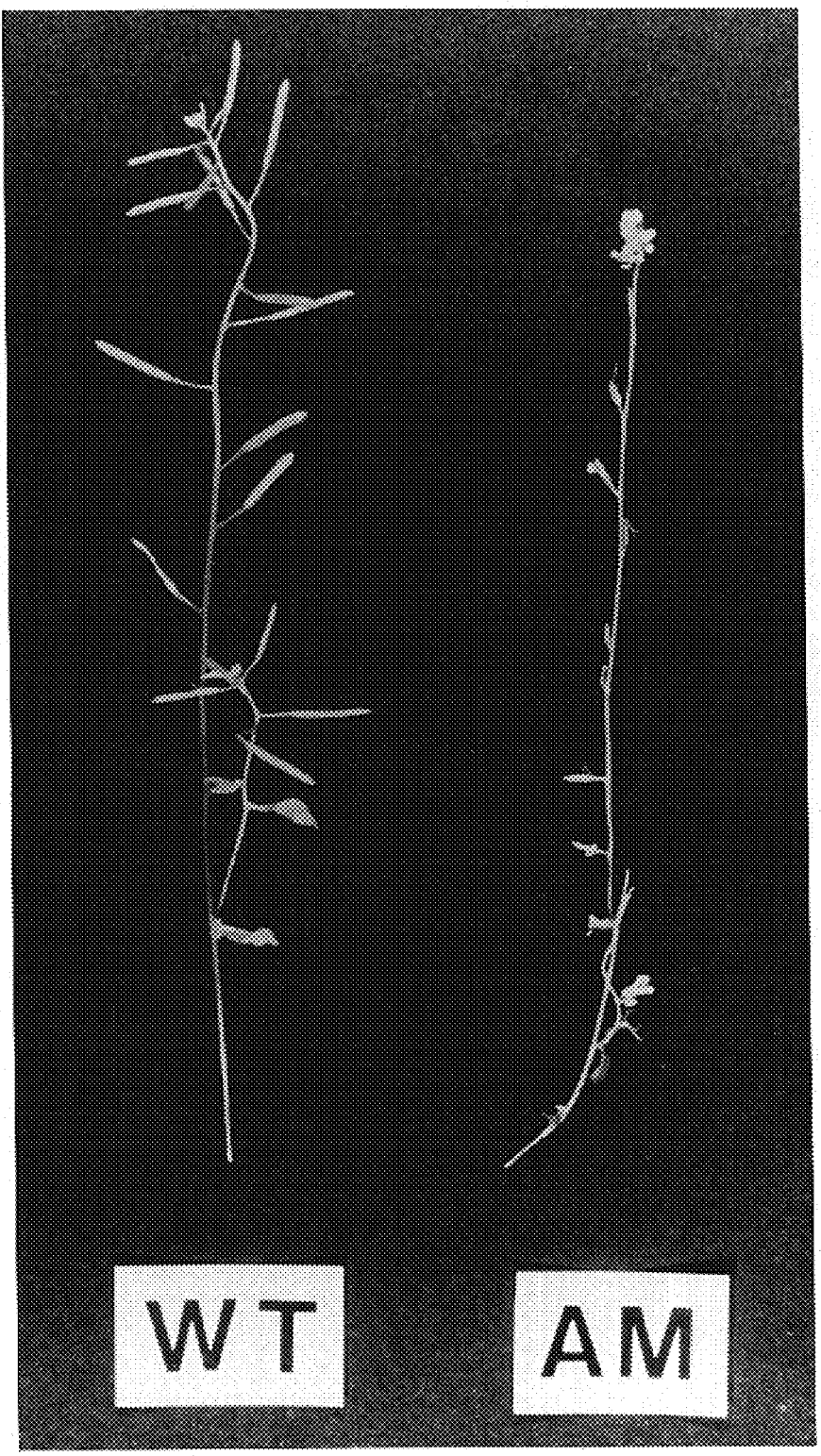
FIG. 9 is a photographic representation of a comprison of *B. campestris* wild type (WT) and an antisense plant (AM) showing appearance of siliques.
Figure 10A:
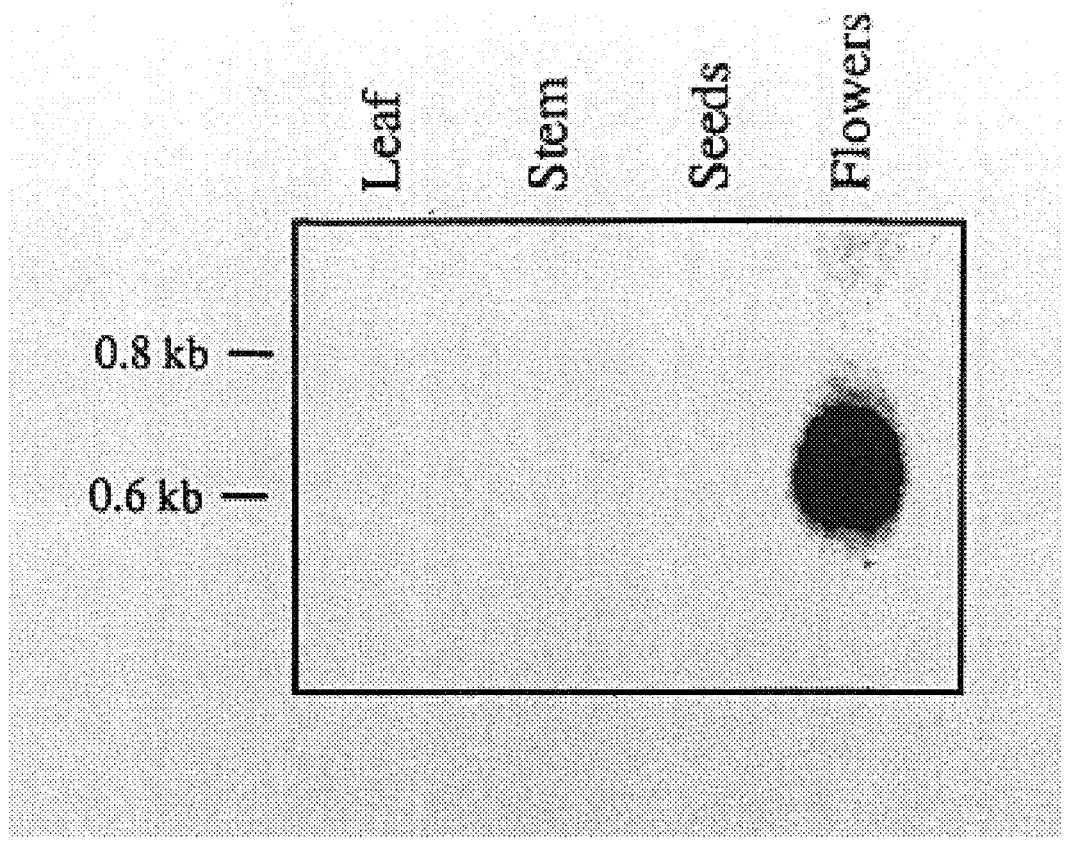
FIGS. 10A–10E are a photographic representations showing tissue-specific expression of the Arabidopsis Bgp1 gene.
Figure 10B:
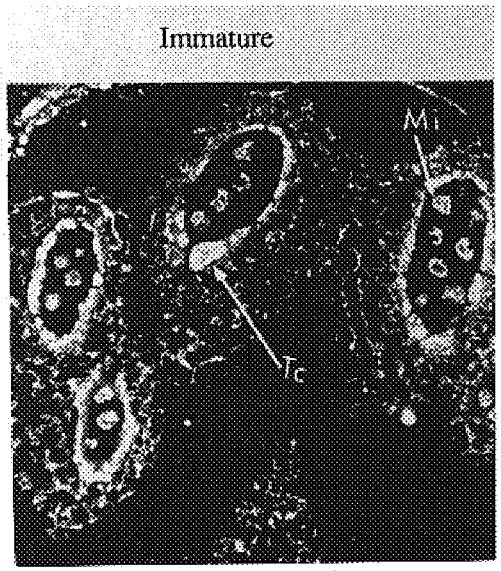
Figure 10C:
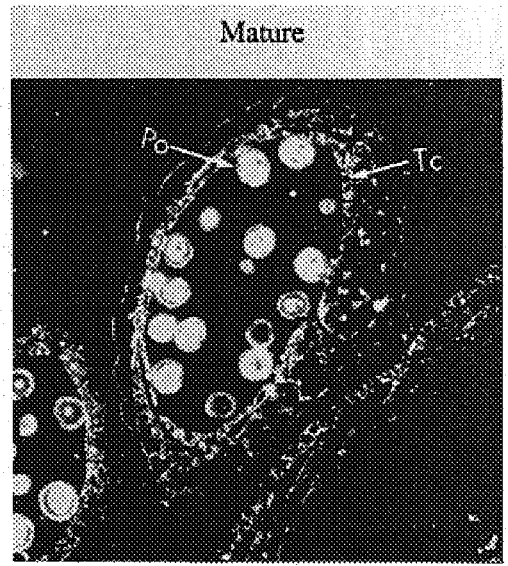
Figure 10D:
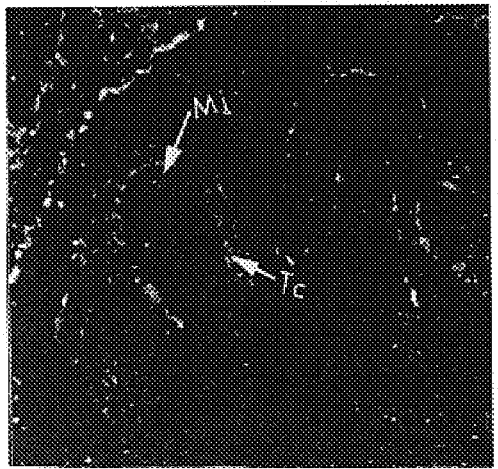
Figure 10E:
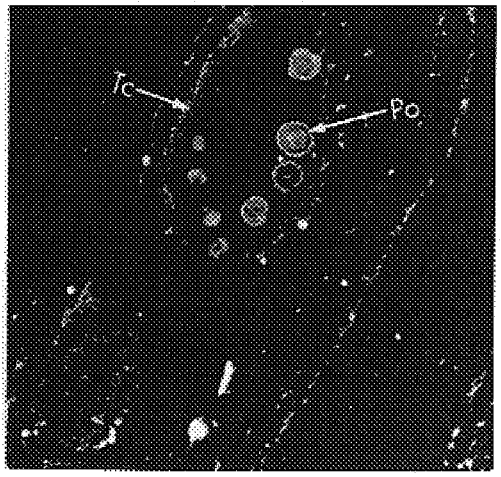

Phenotype Modification of the Transgenic Plants Carrying Bcp1 Antisense Construct The transgenic plants were examined for male-fertility in terms of the number of seeds produced following self-pollination. A total of 50 flowers from each of 20 different healthy plants were examined. All the plants produce phenotypically normal flowers. However, the plant produced short siliques typical of male sterile plants (Moffat and Sommerville, 1988) and no seeds were set after selfing (FIG. 9).

Female-fertility of the Transgenic Plants

The transgenic plants carrying the Bcp1 antisense construct were examined for their female-fertility by cross-pollinating with pollen from Wild-type plants. Ten flowers from three transgenic plants were pollinated with Wild-type pollen. All the flowers produced normal elongated siliques following cross-pollination, indicating that female function is normal in these antisense transgenic plants.

Pollen Morphology in Antisense Plants

Pollen grains from both Wild-type and antisense plants were examined by scanning electron microscopy for possible alteration of pollen surface structure and morphology. Pollen from five of the antisense plants appeared to be collapsed and shrunken when prepared a similar way to wild-type pollen. Some of the pollen grains showed aberrant exine structure. In one antisense plant, the formation of the fish-net patterned ektexine was irregular, with prominent patches where the ektexine was missing over the pollen surface.

In the antisense plants, light and transmission electron microscopic analyses showed that in mature pollen, the internal protoplasmic structure was completely disorganised or empty. Developmental studies showed that tapetal and microspore differentiation was normal until the time of first pollen mitosis. The cytoplasm of the pollen grains then developed mutiple vacuoles, and became disorganised. These data indicate that sterility of the pollen grains sets in at about the time of maximal expression of the gene Bcp1 in the pollen grains. While tapetal development appeared normal, the 100% effectiveness of the antisense construct in all 20 plants suggests that expression of Bgp1 in the tapetum is vital for normal pollen development.

Pollen Viability Test (FCR Test)

Pollen grains from Wild-type and antisense plants were, examined for viability using the Fluorochromatic Reaction (FCR) test (Heslop-Harrison et al., 1984). Pollen from Wild-type gave 99% positive reaction, indicating high pollen quality, whereas pollen from antisense plants showed no positive FCR staining, indicating that pollen quality has been lost, and membrane integrity has been detrimentally altered.

These data show that Bgp1 gene is essential for normal pollen development. This is shown by the male sterility induced when the gene is present in antisense RNA version. Bgp1 is expressed in both the tapetum and pollen, and down regulation of its expression in the antisense plants clearly shows the importance of the gene product for normal development.

EXAMPLE 10

CLONING HOMOLOGOUS GENE FROM ARABIDOPSIS

RNA gel blot studies indicated that a gene homologous to *B. campestris* Bgp1 is expressed in *Arabidopsis thaliana* (FIG. 10). The specificity and pattern of expression in anthers of Arabidopsis Bgp1 was isolated by screening an Arabidopsis genomic library with the Brassica Bgp1 cDNA clone (FIG. 11). DNA sequencing studies show that the Arabidopsis Bgp1 cDNA genomic clone in 1132 bp, with an ORF of 137 amino acids (compared with 119 in Brassica). The deduced amino acid sequence does not contain introns and encodes an alanine-rich (16%) protein with a relative molecular mass, $M_r$ 14K (compared with 12K Brassica). The nucleotide and deduced amino acid sequences of Bgp1 show no homology with other known genes or proteins in the databases. No potential N-glycosylation sites are present in the amino acid sequence. Mouse polyclonal antibodies raised against two synthetic peptides based on hydrophylic regions of the Brassica Bgp1 amino acid sequence recognised $M_r$ 11–12 K polypeptides by Western analysis. Accordingly, the results indicated that the Bgp1 gene is expressed specifically in tapetum and pollen and encodes a protein of $M_r$ 12–14K in both Brassica species and Arabidopsis species.

EXAMPLE 11

CONTROL OF ANTHER-SPECIFIC EXPRESSION OF ARABIDOPSIS Bgp1

To demonstrate that 5' sequences control Bgp1 gene developmental specificity, the *Escherichia coli* GUS gene was fused with a 0.77 kb upstream fragment (nucleotides −767 to +100; Xu et al., 1993), containing the start codon and then transformed Arabidopsis plants with the chimaeric Bgp1 GUS gene. Several independent transformants were obtained. Each transformant showed GUS enzyme activity in both tapetum and pollen. The pattern of GUS activity in anthers of transgenic plants is consistent with the expression of endogenous Bgp1 gene in Brassica and Arabidopsis.

Comparison of 5'-flanking regions of Bgp1 from both Brassica and Arabidopsis shows that the two genes share a conserved region of high homology in the 167 nucleotides that lie immediately upstream of the transcriptional initiation site (FIG. 11b). There is no significant homology between the 5' regions of the two genes beyond this point. Because of the highly conserved pattern of expression of this gene in anthers of the two genera, it was expected that this 167 bp 5' region may be sufficient to direct the normal developmental expression of the genes. To examine this, a chimaeric gene was constructed by fusing the 167 bp fragment with GUS (nucleotides −167 to +100; Xu et al., 1993). The Arabidopsis plants transformed with this construct showed the same pattern of GUS enzyme activity in anthers as those transformed with larger promoter fragments. Since GUS enzyme activity in plants transformed with a truncated 5' fragment appeared to be relatively less than those with the larger fragment, it was decided that the region upstream of the −167 bp may have an enhancer effect for Bgp1 gene expression.

EXAMPLE 12

ANTISENSE INHIBITION OF Bgp1 GENE EXPRESSION INDUCES MALE STERILITY

The 0.77 kb Bgp1 gene regulatory fragment was fused with antisense Bcp1 cDNA expression. This chimaeric construct was introduced into Arabidopsis plants and 22 primary transformants ($T_0$) were obtained. The transformants appeared identical to untransformed control plants with respect to growth rate, height, leaf and flower morphology, time of flowering and flower colour (FIG. 13). However, 7 of antisense transformants failed to show elongation of siliques, indicating loss of fertility.

Microscopic examination of flowers of antisense transformants ($T_0$) showed the presence of defective pollen grains in the anthers, confirming that the effect is specifically on male rather than female fertility. Pollen from anthers of antisense transformants was negative when tested for pollen quality by FCR test (Heslop-Harrison et al., 1984) compared with pollen from anthers of normal plants (FIG. 13). Use of Alexander's stain (which indicates the presence or absence of cytoplasm in pollen grains as a measure of sterility) showed that >90% of pollen in antisense transformants is present as empty exines (green staining), while the remaining grains had cytoplasm (weak pink or red staining) in various stages of degeneration (FIG. 14). In contrast, pollen from anthers of normal plants showed densely staining (purple) grains.

Sections of anthers were prepared from both transformed and untransformed (normal) plants. Male sterile anthers showed collapsed pollen sacs, and pollen grains without visible cytoplasmic contents (FIG. 15a). Rare grains showed some residual cytoplasm that appeared disorganised and lysed (FIG. 15a). All other anther tissues and cell types appeared identical to normal anthers.

DNA gel blot analysis of the male sterile primary transformants showed that the male sterility phenotype is linked with the presence of the antisense cDNA in their genome (FIG. 12a). The presence of the antisense insert was tested both by use of Bgp1 cDNA and neomycin phosphotransferase (NPTII) as hybridisation probes.

To determine whether the male sterility is a stably inherited trait, antisense transformants were crossed with pollen from normal (untransformed) plants. Normal silique formation and seed set occurred in all cases. These results indicate that antisense transformants are male sterile, their pistils are able to recognise and transmit pollen normally, and female fertility is unaffected. Eight of $T_1$ plants were analysed and all inherited the male sterility phenotype. In 4 of 8 $T_1$ plants, the presence of antisense Bgp1 gene was further analysed by DNA gel blot analysis (FIG. 12b). The male sterile phenotype and presence of antisense insert completely co-segregated. The introduced gene is present in the genomic DNA of the analysed $T_1$ plants with male sterile pollen and absent in the genome of $T_1$ plants with normal viable pollen. Inheritance of male sterility phenotype is also observed in $T_2$ generation.

The expression of both endogenous and antisense mRNA expressing Bgp1 in both primary transformants was studied and male sterile $T_1$ plants (FIG. 12c). With sense-specific probe, a single mRNA band of approximately 700 bp was detected in flowers of untransformed plants. The presence of sense Bgp1 mRNA could not be detected in either primary transformed or $T_1$ plants with male sterility phenotype. However, using an antisense-specific probe, a strongly hybridising transcript of approximately 750 bp was detected in flowers of all male sterile transformants. No antisense RNA was detected in control untransformed plants. Thus, the male sterility phenotype is linked with high expression of antisense Bcp1 mRNA and loss of sense Bcp1 mRNA.

EXAMPLE 13

ANTISENSE TRANSFORMANTS SHOW PROGRAMMED CELLULAR AUTOLYSIS DURING POLLEN DEVELOPMENT

In order to define the stage of pollen development when arrest is initiated, thin sections of developing anthers of both normal plants and antisense transformants were prepared. At tetrad and uninucleate microspore stage, both tapetal cells and microspores appeared normal in both types of anthers. This is the stage when tapetum is most active and the exine is completely formed. At the late microspore stage, the microspore cytoplasm showed signs of vacuolation and autolysis (FIG. 14) which appeared to be complete before microspore mitosis. This rapid loss of cellular contents ultimately results in complete collapse of the microspores, which appear as empty shells (FIG. 15), since the exine remains unaffected. The tapetum appeared normal in both types of anther. This developmental sequence was similar in both primary transformants ($T_0$) and male sterile $T_1$ generation.

Those skilled in the art will appreciate that the invention described herein is susceptible to variations and modifications other than those Specifically described. It is to be understood that the invention includes all such variations and modifications. The invention also includes all of the steps, features, compositions and compounds referred to or indicated in this specification, individually or collectively, and any and all combinations of any two or more of said steps or features.

REFERENCES:

Albani D, Robert L S, Donaldson P E, Altosaar I, Arnison P G, Fabijanski S F (1991a) *Plant Mol. Biol.* 15: 605–622.

Albani D, Altosaar I, Arnison P G, Fabijanski S F (1991b) *Plant Mol. Bio.* 16: 501–513.

Alexander M P (1969) *Stain Technology* 44(3): 117–122.

Bevan M, (1984) *Nucl. Acids Res.* 12: 8711–12.

Coleman A, Goff L J (1984) *Stain Techol.* 60:145–154.

Hamilton D A, Bashe D M, Stinson J R, Mascarenhas J P (1989) *Sex. Plant Reprod.* 2:208–212.

Haseloff J and Gerlach L (1988) *Nature* 344: 586–591.

Heslop-Harrison J, Heslop-Harrison Y, Shivanna (1984) *Theor. Appl. Genet.* 67;367–375.

Horsch R B, Fry J E, Hoffmann N L, Wallroth M, Eichholtz D, Rogers S G, Fraley R T (1985) *Science* 227: 1299–1231.

Jefferson R A, Burgess S M, Hirsh D (1986) *Proc. Natl. Acad. Sci. USA* 83:8447–8451.

Jefferson R A, Kavanagh T A, Bevan M W (1987) *EMBO J.* 6:3901–3907.

Koltunow A M, Truettner J, Cox K H, Walroth M, Goldberg R B (1990) *Plant Cell* 2:1201–1224.

Koncz C, Schell J (1986) *Mol. Gen. Genet.* 204:383–396.

Kozak M (1986) *Cell* 44:283–292.

Lutcke H A, Chow K C, Mickel F S, Moss K A, Kern H F, Scheele G A (1987) *EMBO J.* 6: 43–48.

Maniatis T, Fritsch E F, Sambrook J (1982) Molecular Cloning: A Laboratory Manual. Cold Spring Harbour Laboratory Press, New York.

Mascarenhas J P (1988) Anther and pollen expressed genes. In: VermaDPS, Goldberg R B (eds) Temporal and spatial regulation of plant genes. Spriner-Verlag, New York, pp 97–125.

Moffatt B A and Sommerville C (1988) *Plant Physiol.* 86: 1150–1154.

Murray H G, Thompson W F (1980) *Nucl. Acids Res.* 8:4321–4325.

Sambrook et al (1989) Molecular Cloning: A Laboratory Manual. Cold Spring Harbour Laboratory Press, New York.

Theerakulpisut P, Xu H L, Singh M B, Pettitt J M, Knox R B (1991) *Plant Cell.* 3: 1037–1084.

Twell D, Wing R A, Yamaguchi J, McCormick S (1989) *Mol. Gen. Genet.* 217:240–245.

Twell D, Yamaguchi J, Wing R A, Ushiba J, McCormick S (1991) *Genes Dev.* 5:496–507.

Valvekens D, Van Montagu M, Van Lijsebettens M (1988) *Proc. Natl. Acad. Sci.* 85: 5536–5540.

Woodcock D M, Crowther M, Diver W D, Graham M, Bateman C, Baker D J, Smith S S (1988) *Nucl. Acids Res.* 16; 4465–4482.

Xu H (1992) PhD Thesis, University of Melbourne.

Xu H, Davies S P, Kwan B V H, O'Brien A P, Singh, M B, Knox R B (1993) *Mol. Gen. Genet.* 239: 58–65.

What is claimed:

1. A genomic DNA isolate from a plant of Brassica or Arabidopsis comprising:
   (i) a Bgp1 genetic sequence preferentially expressed in anther tissue of a plant and substantially not expressed in non-anther tissue; and
   (ii) an open reading frame having a nucleotide sequence as set forth in SEQ ID NO:1 or having at least 40% similarity thereto.

2. A genomic DNA isolate according to claim 1 wherein the plant is *Brassica campestris* and the nucleotide sequence of the open reading frame is as set forth in SEQ ID NO:1.

3. A genomic DNA isolate according to claim 1 wherein the plant is *Arabidopsis thaliana* and the nucleotide sequence of the open reading frame is set forth in SEQ ID NO. 3.

4. A genomic DNA isolate according to claim 1 further comprising a promoter region 5' to said open reading frame, wherein said promoter region:
   (i) is capable of directing expression in tapetum and/or pollen tissue; and
   (ii) comprises a nucleotide sequence as set forth in SEQ ID NO:5 or having at least 20% similarity thereto.

5. A genomic DNA isolate according to claim 4 comprising a nucleotide sequence as set forth in SEQ ID NO. 3.

6. A genomic DNA isolate comprising an open reading frame, said open reading frame encodes a protein having an amino acid sequence as set forth in SEQ ID NO:2.

7. A genomic DNA isolate comprising an open reading frame, said open reading frame encodes a protein having an amino acid sequence as set forth in SEQ ID NO:4.

* * * * *

UNITED STATES PATENT AND TRADEMARK OFFICE
CERTIFICATE OF CORRECTION

PATENT NO. : 6,740,748 B1
DATED : May 25, 2004
INVENTOR(S) : Robert B. Knox et al.

It is certified that error appears in the above-identified patent and that said Letters Patent is hereby corrected as shown below:

<u>Title page,</u>
Item [73], Assignee, "Univeristy" should read -- University --

Signed and Sealed this

Fourth Day of January, 2005

JON W. DUDAS
*Director of the United States Patent and Trademark Office*

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
      (A) LENGTH: 357 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 1..357

(xi) SEQUENCE DESCRIPTION: SEQ ID NO:1:

```
ATG GGT CGC CAA AAC GCT GTC GTA GTT TTT GGC CTT GTG TTC TTG GCC      48
Met Gly Arg Gln Asn Ala Val Val Val Phe Gly Leu Val Phe Leu Ala
 1               5                  10                  15

ATC CTT GGC CTC GCC GCA GCT GCC TCC TCT CCG TCT CCT TCA GCG TCA      96
Ile Leu Gly Leu Ala Ala Ala Ala Ser Ser Pro Ser Pro Ser Ala Ser
                20                  25                  30

CCC TCC AAA GCT CCG GCT GCT ACC GTA ACC GAT GTC GAA GCT CCA GTG     144
Pro Ser Lys Ala Pro Ala Ala Thr Val Thr Asp Val Glu Ala Pro Val
            35                  40                  45

AGC GAG GAC ACC ATT GGA ACC ACC GAT GAC GAT GCA GCT GCT TCT CCA     192
Ser Glu Asp Thr Ile Gly Thr Thr Asp Asp Asp Ala Ala Ala Ser Pro
        50                  55                  60

GGT GAT GGT GAC GTA GCT GTG GCT GGT CCT CTA GGA AGT GAC TCC TCC     240
Gly Asp Gly Asp Val Ala Val Ala Gly Pro Leu Gly Ser Asp Ser Ser
 65                  70                  75                  80

TAC GGT AGT AAT GGA CCT TCA CCT TCT ACT GAT GCT GCT GAC AGC GGC     288
Tyr Gly Ser Asn Gly Pro Ser Pro Ser Thr Asp Ala Ala Asp Ser Gly
                85                  90                  95

GCG CCT GCT CTT GGC GTC TCT GCG GTC TTC GTT GGT GTT GCA TCC ATC     336
Ala Pro Ala Leu Gly Val Ser Ala Val Phe Val Gly Val Ala Ser Ile
            100                 105                 110

GCC GGT TCT TTC TTG TTT CTC                                         357
Ala Gly Ser Phe Leu Phe Leu
        115
```

(2) INFORMATION FOR SEQ ID NO:2:

(i) SEQUENCE CHARACTERISTICS:
      (A) LENGTH: 119 amino acids
      (B) TYPE: amino acid
      (D) TOPOLOGY: linear (ii) MOLECULE TYPE: protein (xi) SEQUENCE DESCRIPTION: SEQ ID NO:2:

```
Met Gly Arg Gln Asn Ala Val Val Val Phe Gly Leu Val Phe Leu Ala
 1               5                  10                  15

Ile Leu Gly Leu Ala Ala Ala Ala Ser Ser Pro Ser Pro Ser Ala Ser
                20                  25                  30

Pro Ser Lys Ala Pro Ala Ala Thr Val Thr Asp Val Glu Ala Pro Val
            35                  40                  45

Ser Glu Asp Thr Ile Gly Thr Thr Asp Asp Asp Ala Ala Ala Ser Pro
        50                  55                  60
```

```
Gly Asp Gly Asp Val Ala Val Ala Gly Pro Leu Gly Ser Asp Ser Ser
 65                  70                  75                  80

Tyr Gly Ser Asn Gly Pro Ser Pro Ser Thr Asp Ala Ala Asp Ser Gly
                 85                  90                  95

Ala Pro Ala Leu Gly Val Ser Ala Val Phe Val Gly Val Ala Ser Ile
            100                 105                 110

Ala Gly Ser Phe Leu Phe Leu
        115
```

(2) INFORMATION FOR SEQ ID NO:3:

(i) SEQUENCE CHARACTERISTICS:
        (A) LENGTH: 411 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..411

(xi) SEQUENCE DESCRIPTION: SEQ ID NO:3:

```
ATG GGT CGC CAA AAC ATT GTC GTC GTG GTT GCC CTC GTC TTC ATC CGG        48
Met Gly Arg Gln Asn Ile Val Val Val Val Ala Leu Val Phe Ile Arg
 1               5                  10                  15

ATC ATT GGC CTT GCC GCA GCT GCC TCC TCT CCA TCT CCT TCA GCG TCT        96
Ile Ile Gly Leu Ala Ala Ala Ala Ser Ser Pro Ser Pro Ser Ala Ser
             20                  25                  30

CCC TCC AAA GCT CCA GCT GCC TCC AAA ACC GAT CAT GTC GAG GCT CCA       144
Pro Ser Lys Ala Pro Ala Ala Ser Lys Thr Asp His Val Glu Ala Pro
         35                  40                  45

GTC ACC GAT GAC CAA ATC GGA ACC ACC GAT GAC GAT GCA GCT CCT ACT       192
Val Thr Asp Asp Gln Ile Gly Thr Thr Asp Asp Asp Ala Ala Pro Thr
     50                  55                  60

CCT GGT GAC GGT GAC GTT GCA GTG GCT GGT CCT CTA GGA AGT GAC TCC       240
Pro Gly Asp Gly Asp Val Ala Val Ala Gly Pro Leu Gly Ser Asp Ser
 65                  70                  75                  80

TCG TAC GAC AAT GCC GCT ACA GGC TCT GCT GAT TCT GCC AAA AGC GGT       288
Ser Tyr Asp Asn Ala Ala Thr Gly Ser Ala Asp Ser Ala Lys Ser Gly
                 85                  90                  95

GCG GCA GCT CTT GGC GTC TCT GCG GTC GTC GTT GGT GTT ACA TCA TTG       336
Ala Ala Ala Leu Gly Val Ser Ala Val Val Val Gly Val Thr Ser Leu
            100                 105                 110

CTG GTT CTT TCT TGT TAC TCA AGT TGG GCA TTG TTT TAT GAT AAG AAG       384
Leu Val Leu Ser Cys Tyr Ser Ser Trp Ala Leu Phe Tyr Asp Lys Lys
        115                 120                 125

GTT ATT TTA AAC GAA GAT TAT TAT ATG                                   411
Val Ile Leu Asn Glu Asp Tyr Tyr Met
    130                 135
```

(2) INFORMATION FOR SEQ ID NO:4:

(i) SEQUENCE CHARACTERISTICS:
        (A) LENGTH: 137 amino acids
        (B) TYPE: amino acid
        (D) TOPOLOGY: linear (ii) MOLECULE TYPE: protein (xi) SEQUENCE DESCRIPTION: SEQ ID NO:4:

Met Gly Arg Gln Asn Ile Val Val Val Val Ala Leu Val Phe Ile Arg

```
 1               5                  10                 15
Ile Ile Gly Leu Ala Ala Ala Ser Ser Pro Ser Pro Ser Ala Ser
                20              25              30

Pro Ser Lys Ala Pro Ala Ala Ser Lys Thr Asp His Val Glu Ala Pro
        35              40              45

Val Thr Asp Asp Gln Ile Gly Thr Thr Asp Asp Ala Ala Pro Thr
        50              55              60

Pro Gly Asp Gly Asp Val Ala Val Ala Gly Pro Leu Gly Ser Asp Ser
65              70              75              80

Ser Tyr Asp Asn Ala Ala Thr Gly Ser Ala Asp Ser Ala Lys Ser Gly
                85              90              95

Ala Ala Ala Leu Gly Val Ser Ala Val Val Gly Val Thr Ser Leu
            100             105             110

Leu Val Leu Ser Cys Tyr Ser Ser Trp Ala Leu Phe Tyr Asp Lys Lys
        115             120             125

Val Ile Leu Asn Glu Asp Tyr Tyr Met
130             135
```

(2) INFORMATION FOR SEQ ID NO:5:

(i) SEQUENCE CHARACTERISTICS:
        (A) LENGTH: 838 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

```
TATCATTCCT TTAATTTCAA GGAATTATAG AACAAAAAAT GTTCTTTATA AAAATTAAGA    60
AGGAACAAGG GATTCATTCC TACTATTCTG TTCTTGGTCA TTATTTTCCT CTTCATTCAT   120
ATTGTTTCTT TAATTGTTAC CAATTAGAAC TTTAACGAAT AAATAGTTAA TTCGTATTAT   180
GAGATTTACA CAATTCTTAT TCACTCAATT TGGAGTTTTA AAGATTTTTT AAAAGATTTA   240
TGGTGGGAAC CTTCTTCTTT TCTTATTTAT CATGATGATG ATAACCTTCC CAGCAGAATT   300
ATTCTTAGAA CTTTTTTTCA CATTTAGGTA TCCATGCCTA AGTAAGGCTT AGTTAAAGAT   360
GTTTTATAAA CTTTGATCAA AATATTCATT CAATTAATTT GAGCTTCAAC TATAAATTGT   420
TGTATGCATT CGTTTTAGCC TGTAAGATAT CAGACATTCA CGTTTCGATA AACAAGTATA   480
TAAATAATAT GAATATTGTA CATTCATTTT ATTCGGTTCA TCAACCAAAA AAAATAAAAA   540
TAAATATTCG TATTCATCTA TGCTTTGGCA TGGTCCGTTC TTTTTTCTTG ATTGGCTCGT   600
TACCATTCAA AAATATATAC CTTAGCAAAC CCATTTTTAG ACATTCCAGT TGATCTACAT   660
TAGATTGAAC GGTATTCCTC CTACGTAGTA AGAACGTTTT CTATTTTTCT TTGTTTCAGT   720
CATACAACAC AACTATATAT ACACAGCAAC CCCATCTCCT CTCCAATCAT CACAATCTCT   780
AACGTTAAAC CCTAAGACAA ACTAAAAGAG AGCTACGTAC AAGGAGACAG AGAGAAGA    838
```

(2) INFORMATION FOR SEQ ID NO:6:

(i) SEQUENCE CHARACTERISTICS:
        (A) LENGTH: 496 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

```
AAAAGCGAGA AGAAGAAGTC TGGAAGATTT GAGAGCTTAA AGTGGTCGAG TGTAAAACCC      60

TAACTCGCTG TTGATGGCAG AATCGTAAAT CGGAATTGAT TCATGGGCCT AACAAGACGT     120

TTGGGCTTAT GGGTTTAAAG CCCATCTGAT ATAAGATGAA TAGAATGTTC ATGGCAATAC     180

TATCATAATT TGGTTCTTTA ATAAGACACT CGTTAATACG ACGACGATTT GAAGTTGAAC     240

GAATGTTTTC ATATTCATTC GCATGTTCAC CAATCAAAAT CTATATCTGA ACAAGTCCAT     300

TTTTAGGTAC TCCAGTAGAT TTACATTGGA TTGTAAGGTA ATCCTACATC TTAGTTCACG     360

TTTTCTATTT TTGGTCTTGT CACTAAACAC AACTATATAT ACATATCAAA CTCATCTTCG     420

GAAATCATCA CAATCAATAA ACCTCAAACC CTAAAATAAA TTAAACGAGT TCTACGTAAG     480

AAGGAGAGAG AGAAGA                                                     496
```

(2) INFORMATION FOR SEQ ID NO:7:

(i) SEQUENCE CHARACTERISTICS:
        (A) LENGTH: 1621 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

```
TATCATTCCT TTAATTTCAA GGAATTATAG AACAAAAAAT GTTCTTTATA AAAATTAAGA      60

AGGAACAAGG GATTCATTCC TACTATTCTG TTCTTGGTCA TTATTTTCCT CTTCATTCAT     120

ATTGTTTCTT TAATTGTTAC CAATTAGAAC TTTAACGAAT AAATAGTTAA TTCGTATTAT     180

GAGATTTACA CAATTCTTAT TCACTCAATT TGGAGTTTTA AAGATTTTTT AAAAGATTTA     240

TGGTGGGAAC CTTCTTCTTT TCTTATTTAT CATGATGATG ATAACCTTCC CAGCAGAATT     300

ATTCTTAGAA CTTTTTTTCA CATTTAGGTA TCCATGCCTA AGTAAGGCTT AGTTAAAGAT     360

GTTTTATAAA CTTTGATCAA AATATTCATT CAATTAATTT GAGCTTCAAC TATAAATTGT     420

TGTATGCATT CGTTTTAGCC TGTAAGATAT CAGACATTCA CGTTTCGATA AACAAGTATA     480

TAAATAATAT GAATATTGTA CATTCATTTT ATTCGGTTCA TCAACCAAAA AAAATAAAAA     540

TAAATATTCG TATTCATCTA TGCTTTGGCA TGGTCCGTTC TTTTTTCTTG ATTGGCTCGT     600

TACCATTCAA AAATATATAC CTTAGCAAAC CCATTTTTAG ACATTCCAGT TGATCTACAT     660

TAGATTGAAC GGTATTCCTC CTACGTAGTA AGAACGTTTT CTATTTTTCT TTGTTTCAGT     720

CATACAACAC AACTATATAT ACACAGCAAC CCCATCTCCT CTCCAATCAT CACAATCTCT     780

AACGTTAAAC CCTAAGACAA ACTAAAAGAG AGCTACGTAC AAGGAGACAG AGAGAAGAAT     840

GGGTCGCCAA AACGCTGTCG TAGTTTTTGG CCTTGTGTTC TTGGCCATCC TTGGCCTCGC     900

CGCAGCTGCC TCCTCTCCGT CTCCTTCAGC GTCACCCTCC AAAGCTCCGG CTGCTACCGT     960

AACCGATGTC GAAGCTCCAG TGAGCGAGGA CACCATTGGA ACCACCGATG ACGATGCAGC    1020

TGCTTCTCCA GGTGATGGTG ACGTAGCTGT GGCTGGTCCT CTAGGAAGTG ACTCCTCCTA    1080

CGGTAGTAAT GGACCTTCAC CTTCTACTGA TGCTGCTGAC AGCGGCGCGC CTGCTCTTGG    1140

CGTCTCTGCG GTCTTCGTTG GTGTTGCATC CATCGCCGGT TCTTTCTTGT TTCTCTGAGG    1200

TGTGTATTAT CATGAGAAGA TTATTCTGAC TGAAGACTAT TAATATGTAT GGATGATTGT    1260

GATGGTCGTG TTGTAATATG TTTCTCCTTT ATTGTGAGAA ACGATGTTTT GCTAATAAAA    1320

CTGAAAAAAA AAACGAAAAT TTCCTCTAGC CAAGGATAAA ATGCCGGAAT TGCGGATTAA    1380

ATAGTACTAT TCAATCCTTT CATGTTTTCG AGATACAAAA ATACATATTA ATCAGGTAGA    1440
```

```
GCCGTAGAAG TCCGTAACCA CTGGATACAA TCTTTTTCGT AGTAAGAAAG AAAGTACAAT    1500

CTTATTCTAA ATGCATGTGT TTGATAGATT ATGGAACGGT GAGAAGGGCA TTGATTATGG    1560

GAGTTATGAT CGAAGATACA CACGATACCA TCTTTTTAGG TATAGCTTCT TCTTCTATAA    1620

A                                                                    1621
```

(2) INFORMATION FOR SEQ ID NO:8:

(i) SEQUENCE CHARACTERISTICS:
        (A) LENGTH: 1132 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

```
AAAAGCGAGA GAAGAAGTC TGGAAGATTT GAGAGCTTAA AGTGGTCGAG TGTAAAACCC      60

TAACTCGCTG TTGATGGCAG AATCGTAAAT CGGAATTGAT TCATGGGCCT AACAAGACGT    120

TTGGGCTTAT GGGTTTAAAG CCCATCTGAT ATAAGATGAA TAGAATGTTC ATGGCAATAC    180

TATCATAATT TGGTTCTTTA ATAAGACACT CGTTAATACG ACGACGATTT GAAGTTGAAC    240

GAATGTTTTC ATATTCATTC GCATGTTCAC CAATCAAAAT CTATATCTGA ACAAGTCCAT    300

TTTTAGGTAC TCCAGTAGAT TTACATTGGA TTGTAAGGTA ATCCTACATC TTAGTTCACG    360

TTTTCTATTT TTGGTCTTGT CACTAAACAC AACTATATAT ACATATCAAA CTCATCTTCG    420

GAAATCATCA CAATCAATAA ACCTCAAACC CTAAAATAAA TTAAACGAGT TCTACGTAAG    480

AAGGAGAGAG AGAAGAATGG GTCGCCAAAA CATTGTCGTC GTGGTTGCCC TCGTCTTCAT    540

CCGGATCATT GGCCTTGCCG CAGCTGCCTC CTCTCCATCT CCTTCAGCGT CTCCCTCCAA    600

AGCTCCAGCT GCCTCCAAAA CCGATCATGT CGAGGCTCCA GTCACCGATG ACCAAATCGG    660

AACCACCGAT GACGATGCAG CTCCTACTCC TGGTGACGGT GACGTTGCAG TGGCTGGTCC    720

TCTAGGAAGT GACTCCTCGT ACGACAATGC CGCTACAGGC TCTGCTGATT CTGCCAAAAG    780

CGGTGCGGCA GCTCTTGGCG TCTCTGCGGT CGTCGTTGGT GTTACATCAT TGCTGGTTCT    840

TTCTTGTTAC TCAAGTTGGG CATTGTTTTA TGATAAGAAG GTTATTTTAA ACGAAGATTA    900

TTATATGTAA GGATGATTGT GATGATCCGT TGACCTGCAG GTCGACCCAG ATCCGCCTAC    960

CTTTCACGAG TTGCGCAGTT TGTCTGCAAG ACTCTATGAG AAGCTGATAA GAGATAAGTT   1020

TGCTCAACAT CTTCTCGGGC ATAAGTCCGG ACACCATGGC ATCACAGTAT CGAGATGACA   1080

GAGGCAGGGA GTGGACAAA ATTGAAATCA AATGATCGAT TTTATTTTGG CT           1132
```

(2) INFORMATION FOR SEQ ID NO:9:

(i) SEQUENCE CHARACTERISTICS:
        (A) LENGTH: 652 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

```
TATCATTCCT TTAATTTCAA GGAATTATAG AACAAAAAAT GTTCTTTATA AAAATTAAGA     60

AGGAACAAGG GATTCATTCC TACTATTCTG TTCTTGGTCA TTATTTTCCT CTTCATTCAT    120

ATTGTTTCTT TAATTGTTAC CAATTAGAAC TTAACGAATA AATAGTTAAT TCGTATTAT    180
```

-continued

```
GAGATTTACA CAATTCTTAT TCACTCAATT TGGAGTTTTA AAGATTTTTT AAAAGATTTA    240

TGGTGGGAAC CTTCTTCTTT TCTTATTTAT CATGATGATG ATAACCTTCC CAGCAGAATT    300

ATTCTTAGAA CTTTTTTTCA CATTTAGGTA TCCATGCCTA AGTAAGGCTT AGTTAAAGAT    360

GTTTTATAAA CTTTGATCAA AATATTCATT CAATTAATTT GAGCTTCAAC TATAAATTGT    420

TGTATGCATT CGTTTTAGCC TGTAAGATAT CAGACATTCA CGTTTCGATA AACAAGTATA    480

TAAATAATAT GAATATTGTA CATTCATTTT ATTCGGTTCA TCAACCAAAA AAAATAAAAA    540

TAAATATTCG TATTCATCTA TGCTTTGGCA TGGTCCGTTC TTTTTTCTTG ATTGGCTCGT    600

TACCATTCAA AAATATATAC CTTAGCAAAC CCATTTTTAG ACATTCCAGT TG            652
```

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Oligonucleotide DNA (xi) SEQUENCE DESCRIPTION: SEQ ID NO:10:

```
GGCTGCTACC GTAACCGATG T                                              21
```

(2) INFORMATION FOR SEQ ID NO:11:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: Oligonucleotide DNA (xi) SEQUENCE DESCRIPTION: SEQ ID NO:11:

```
CGTTTTGGCG ACCCA                                                     15
```

(2) INFORMATION FOR SEQ ID NO:12:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: Oligonucleotide DNA (xi) SEQUENCE DESCRIPTION: SEQ ID NO:12:

```
CAACTATATA TAG                                                       13
```

(2) INFORMATION FOR SEQ ID NO:13:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: Oligonucleotide DNA (xi) SEQUENCE DESCRIPTION: SEQ ID NO:13:

```
AACAATGGC                                                             9
```